United States Patent [19]

Kusakabe et al.

[11] Patent Number: 4,614,714

[45] Date of Patent: Sep. 30, 1986

[54] USE OF NOVEL L-GLUTAMIC ACID OXIDASE

[75] Inventors: Hitoshi Kusakabe; Hiroshi Yamauchi; Yuichiro Midorikawa, all of Choshi, Japan

[73] Assignee: Yamasa Shoyu Kabushiki Kaisha, Chiba, Japan

[21] Appl. No.: 509,234

[22] Filed: Jun. 28, 1983

[30] Foreign Application Priority Data

Aug. 21, 1982 [JP] Japan ............................... 57-145346
Aug. 23, 1982 [JP] Japan ............................... 57-146707

[51] Int. Cl.$^4$ .......................... C12Q 1/26; C12N 9/06; C12M 1/40; C12M 1/34
[52] U.S. Cl. ..................................... 435/25; 435/191; 435/288; 435/291; 435/810; 435/817
[58] Field of Search ................. 435/25, 191, 291, 810, 435/817

[56] References Cited

FOREIGN PATENT DOCUMENTS 57-43685  3/1982  Japan ................................. 435/191

Primary Examiner—Lionel M. Shapiro
Attorney, Agent, or Firm—Wenderoth, Lind & Ponack

[57] ABSTRACT

The present invention consists of an analytical method for assay of L-glutamic acid in a sample by the use of an L-glutamic acid oxidase which is an L-amino acid oxidase catalyzing the oxidative deamination of the $\alpha$-amino group of L-glutamic acid in the presence of water and oxygen to form $\alpha$-ketoglutaric acid, ammonia and hydrogen peroxide, and having a very high substrate specificity for L-glutamic acid substantially without acting on L-glutamine and L-histidine, and also having a high stability, a reagent for analysis to practice the analytical method, a kit for analysis comprising the reagent, and a biosensor employing the enzyme.

10 Claims, 24 Drawing Figures ature of the Art
This invention relates to the use of a novel L-glutamic acid oxidase, particularly to the use thereof for analysis of L-glutamic acid.

More specifically, the present invention relates to an analytical method for assay of L-glutamic acid in a sample to be analyzed by the use of a novel L-glutamic acid oxidase which exhibits a strong affinity and a high substrate specificity for L-glutamic acid but has substantially no action on other amino acids and yet has a high stability, a reagent for analysis to practice the analytical method, a kit for analysis comprising the reagent, and a biosensor employing the enzyme.

2. Prior Art

As methods for analysis of L-glutamic acid, the chromatographic method, the microbiological quantitative determination method, the electrophoresis method, and the enzymatic method have been known. Among these methods, the chromatographic method and the enzymatic method are most generally used.

As the chromatographic method, the method in which an amino acid autoanalyzer is employed is generally practiced. This method, while it is an excellent method of high precision as well as high reliability, uses an expensive apparatus and may also involve a problem in that deproteinization may be sometimes required depending on the sample, thus making the method for sample preparation complicated.

The enzymatic methods known in the art are (1) the method in which an L-glutamic acid decarboxylase is used and (2) the method in which an L-glutamic acid dehydrogenase is used. However, the methods employing these enzymes have the following problems.

In the method (1) wherein an L-glutamic acid decarboxylase is employed, measurement of the amount of L-glutamic acid is carried out by detection of carbon dioxide which is the reaction product, for which there is generally employed (a) the method using a Warburg manometer or (b) the method using an autoanalyzer.

The method (a) using a Warburg manometer affords high precision, but it requires considerable skill of an expert, takes a long time for measurement, and also has a low sample-processing capacity. On the other hand, in the method (b) using an autoanalyzer, carbon dioxide is absorbed in a sodium carbonate solution of phenolphthalein, and the amount of carbon dioxide generated is measured by the degree of color reduction. Therefore preliminary treatments such as degassing of carbon dioxide and oxygen from an enzyme solution and a buffer are required under cooling, and also gas-liquid separation is necessary after the reaction, whereby the apparatus becomes disadvantageously complicated.

According to this enzymatic method, as an L-glutamic acid decarboxylase, an enzyme obtained from a pumpkin or *E. coli* is generally used. The enzyme from a pumpkin has a urease activity, and therefore when a sample containing urea is to be measured, measurement errors due to carbon dioxide from the urea may occur. The activity of this enzyme is also inhibited by an organic acid such as acetic acid, etc., and therefore, when a sample contains a large amount of organic acids, the enzymatic activity may be inhibited by the acids contained in the sample to provide inaccurate results. On the other hand, an enzyme from *E. coli* exhibits activities for L-arginine and L-glutamine, and therefore an accurate result cannot be obtained for a sample containing such a large amount of these amino acids as to have a substantial influence on the analysis of L-glutamic acid. Also, storage stability of the enzyme per se is not good.

The L-glutamic acid dehydrogenase used in the method (2) catalyzes the reaction in which L-glutamic acid is deaminated in the presence of NAD (oxidized form of nicotinamide adenine dinucleotide) to form α-ketoglutaric acid and ammonia accompanied with the formation of NADH (reduced form of nicotinamide adenine dinucleotide). In the method using this enzyme, measurement of the reaction is conducted by detection of the amount of NADH formed through the increase in absorbance at 340 nm. However, the equilibrium in this enzymatic reaction is more inclined toward formation of L-glutamic acid, and, for analysis of L-glutamic acid by the use of this enzyme, the equilibrium of this reaction must be shifted toward formation of α-ketoglutaric acid, and various contrivances are required therefor. For this purpose, a trapping agent for α-ketoglutaric acid is generally added to the reaction system, but such an agent may sometimes interfere with the reaction unless its concentration is strictly controlled. Further, the NAD concentration must also be controlled strictly. In the case of measuring a sample containing a substance exhibiting absorption at the wavelength to be measured, such as soy sauce, the value obtained must be corrected by using the value obtained in a blank test. Also, a lactic acid dehydrogenase may sometimes exist in the enzyme employed, and the influence of such an enzyme must also be taken into consideration.

Recently, an L-amino acid oxidase having a substrate specificity for L-glutamic acid has been found to be produced by cultivation of a microorganism belonging to the genus Streptomyces (hereinafter sometimes abbreviated as "S."), more specifically *Streptomyces violascens* (See Japanese Patent Laid-Open Publication No. 43685/1982). The physicochemical properties of the glutamic acid oxidase (hereinafter sometimes abbreviated as "known enzyme") as a protein have not yet been clarified, but the known enzyme is described to have enzymological properties as follows.

(1) Substrate specificity

When the velocity of enzymatic reaction for L-glutamic acid is given as 100, the known enzyme has a relative activity of 8.4 for L-glutamine and 6.8 for L-histidine, exhibiting substantially no activity for other amino acids.

(2) Optimum pH pH 5-6

(3) pH stability

Stable in the range of pH 3.5-6.5 (37° C., maintained for one hour)

(4) Temperature stability

Stable up to 50° C. (maintained for 10 minutes) (5) Influence of inhibitors

Substantially completely inhibited by mercury ions, copper ions and diethyldithiocarbamate.

The specification of the above Laid-Open Publication states that a liquid culture of the aforesaid microorganism is preferable for production of the known enzyme.

For utilization of the known enzyme for analysis of L-glutamic acid, various problems are involved. Specifically, although the known enzyme has a higher substrate specificity for L-glutamic acid as compared with L-amino acid oxidases known in the art, it still exhibits clear activities for other amino acids as mentioned above, and therefore it cannot be used for specific quantitative determination of L-glutamic acid in the presence of these amino acids. Also, the known enzyme does not have a high pH stability and heat stability, and it cannot be considered to always have a good storage stability and stability during use as a reagent for analysis. Further, when copper ions exist in a sample to be analyzed, the activity of the known enzyme is markedly inhibited, whereby analysis may be considered to become difficult. Furthermore, the pH of reaction solutions employed in various clinical biochemical diagnostic analysis, especially in analysis of the activity of enzymes in blood, is usually around neutral, while the known enzyme will completely lose its activity at a pH of 7.5 when treated at 37° C. for one hour. For this reason, it may be difficult to use the known enzyme in analysis around the neutral pH range.

The method for analysis of L-amino acid by the use of an L-amino acid oxidase has been known in the prior art, but it is difficult for known L-amino acid oxidases to act on L-glutamic acid, and therefore no specific analysis of L-glutamic acid has been possible according to the method in which such an enzyme is employed.

On the other hand, as another measure for analysis of L-glutamic acid, the method using a biosensor is known.

In the prior art, known biosensors for analysis of L-glutamic acid include (1) an enzyme electrode using L-glutamic acid dehydrogenase as the receptor portion of L-glutamic acid and a cation electrode as the transducer portion [Anal. Chim. Acta, 56, 333 (1971)] and (2) a microorganism electrode using the lyophilized cell of E. coli, which exhibits L-glutamic acid decarboxylase activity, as the receptor portion of L-glutamic acid and a carbon dioxide electrode as the transducer portion [Anal. Chim. Acta, 116, 61 (1980)].

The enzyme electrode of (1) is not practical since it has an extremely poor stability of the enzyme (only for 2 days) and also is susceptible to the influence of cations coexisting in the same measurement system such as sodium ion and potassium ion because of the use of a cation electrode. The microorganism electrode of (2) has an excellent stability (for 3 weeks, 1,500 times or more) because an immobilized microorganism cell is employed. However, carbon dioxide is generated through the aspiration action of the cell under aerobic conditions to exert an influence on the measurement. For removal of such an influence, it is necessary to inhibit the aspiration action of the cell and also to remove carbon dioxide contained in the sample by, for example, blowing nitrogen gas into the reaction mixture. Also, since the microorganism electrode does not have a high substrate specificity as tabulated below, it can be utilized only for rough measurements as in a process control of fermentation.

| Substrate Specificity Microorganism Electrode | |
|---|---|
| Amino acid | Relative sensitivity ratio |
| Glutamic acid | 100 |
| Glutamine | 108 (11*) |
| Alanine | 0.5 |
| Arginine | 0.6 |
| Aspartic acid | 1.0 |
| Cystine | 0.4 |
| Glycine | 0.4 |

| -continued | |
|---|---|
| Substrate Specificity Microorganism Electrode | |
| Amino acid | Relative sensitivity ratio |
| Tryptophan | 0.4 |

*Acetone treated cell was employed.

An enzyme electrode using an L-amino acid oxidase as the receptor portion is also known [Anal. Chem., 47, 1359 (1975)]. However, the L-amino acid oxidase of the prior art used in such an enzyme electrode acts on L-glutamic acid to a very small extent, and no specific analysis of L-glutamic acid has heretofore been possible by the use of the above enzyme electrode.

There is no disclosure in the above Laid-Open Publication as to whether or not the aforesaid known enzyme can be utilized for a biosensor for specific analysis of L-glutamic acid. Even if the known enzyme can be utilized as the receptor portion of a biosensor, it is possible for various problems to arise. That is, the known enzyme, while it has a relatively higher substrate specificity for L-glutamic acid as compared with L-amino acid oxidases known in the prior art, still exhibits clear activities for other amino acids as mentioned above, and therefore it cannot be utilized as the biosensor for specific analysis of L-glutamic acid in the co-presence of these amino acids. Also, the known enzyme does not have a high stability, and it cannot be considered to necessarily have a good storage stability and stability during use when utilized as the receptor portion of the biosensor. Further, since the known enzyme is extremely unstable in the pH range above 7 it may be difficult to use the known enzyme biosensor around the neutral pH range in which various biochemical analyses in the clinical field should be carried out. Furthermore, when copper ions are present in a sample to be analyzed, the activity of the known enzyme may be considered to be markedly inhibited by such ions, whereby analysis becomes difficult.

As described above, there has been in the prior art neither a biosensor for analysis of L-glutamic acid utilizing an oxidase as the receptor portion for specific recognition of L-glutamic acid nor an L-amino acid, oxidase capable of accomplishing sufficiently such an object.

SUMMARY OF THE INVENTION

We have found that a novel L-glutamic acid oxidase discovered by some of us from the cultured product of an actinomycete newly isolated from a soil sample can oxidatively deaminate specifically L-glutamic acid in the presence of given amounts of water and oxygen to form quantitatively α-ketoglutaric acid, ammonia and hydrogen peroxide. On the basis of this finding, we have arrived at the present invention.

The present invention provides a method for analysis of L-glutamic acid, which comprises allowing the novel L-glutamic acid oxidase to react with L-glutamic acid in the presence of oxygen and water, and detecting the consumption of oxygen or formation of hydrogen peroxide, ammonia or α-ketoglutaric acid accompanying the reaction.

In accordance with the present invention there is also provided a method for analysis of L-glutamic acid, which comprises allowing the novel L-glutamic acid oxidase to react with L-glutamic acid at pH 5-6 in the presence of oxygen and water in the case of a sample containing such a large amount of L-aspartic acid as to have a substantial influence on the analysis of L- glutamic acid, and detecting the consumption of oxygen or formation of hydrogen peroxide, ammonia or α-ketoglutaric acid accompanying the reaction.

The present invention also provides a reagent for analysis of L-glutamic acid comprising the novel L-glutamic acid oxidase.

Further, the present invention provides a kit for analysis of L-glutamic acid comprising the novel L-glutamic acid oxidase and a detective reagent for the reaction by the enzyme.

The present invention also provides a biosensor comprising a receptor portion for a substance to be detected comprising an enzyme and a transducer portion which detects the chemical or physical change in a sample to be analyzed through the action of the enzyme and converts it to an electric signal, wherein there is used as the enzyme the novel L-glutamic acid oxidase which has a very high substrate specificity for L-glutamic acid substantially without action on amino acids other than L-glutamic acid, and also has a high stability.

Meritorious effects

The novel L-glutamic acid oxidase (hereinafter sometimes abbreviated as "novel enzyme") acts specifically on L-glutamic acid substantially without action on other amino acids, and therefore it is suitable for quantitative determination of L-glutamic acid in a system containing many kinds of amino acids. Its specificity for L-glutamic acid is so high that no pre-treatment whatsoever of the sample, such as fractionation of amino acids in the sample, is required in carrying out the analysis. For example, it can be used for simple, rapid and specific measurement of glutamic acid content in foods containing many kinds of amino acids such as soy sauce, extracts, liquid seasonings, etc., the glutamic acid content being an important index in quality evaluation, for process control or process analysis in such fields as glutamic acid fermentation and production of soy sauce, and for screening of glutamic acid producing microorganisms. Also, since activity assays of enzymes forming glutamic acid as the product such as glutaminase, glutamic acid-oxaloacetic acid transaminase (GOT), glutamic acid-pyruvic acid transaminase (GPT), and γ-glutamyl transpeptidase (γ-GTP) can easily be done by the use of the novel enzyme, this enzyme is useful in clinical diagnosis or in the field of biochemistry.

The novel enzyme also has an advantage in the assay of its enzyme activity since its enzymatic reaction is an oxidase reaction most widely practiced in clinical diagnosis or food analysis.

Further, the novel enzyme has a high stability when compared with enzymes for analysis in general including known enzymes, and therefore it can be utilized as an enzyme electrode for a glutamic acid sensor. It can also be expected to be utilized as a labelling enzyme in enzyme immunoassay (see Japanese Patent Laid-Open Publication No. 37261/1982), and further, the reagent for analysis of the present invention is stable in storage and use, resulting in general applicability and economical advantage.

The biosensor of the present invention, differing from the known biosensors for analysis of L-glutamic acid, employs an oxidase which is most widely used as the receptor portion of a biosensor, and therefore it can be manufactured very easily. Furthermore, the detecting means of the enzymatic reaction may be chosen from a variety of means known in the art depending on its purpose, such as a means for detecting reduction of oxygen which is a substrate, or a means for detecting increase of hydrogen peroxide or ammonia which is the reaction product. Further, the biosensor of the present invention has far higher specificity for L-glutamic acid as compared with the known biosensors and therefore can be used for analyzing only L-glutamic acid selectively without interference by other amino acids, even in a sample containing many kinds of amino acids.

By the use of the biosensor of the present invention as described above, not only can L-glutamic acid be analyzed in samples for analysis containing L-glutamic acid as its essential component such as foods, fermented liquors and others, but it is also possible to analyze enzyme activities or other substances concerned with the enzyme reaction in which L-glutamic acid is liberated, for example, in the reaction systems of glutaminase, glutamic acid recemase, glutamic acid-oxaloacetic acid transaminase (GOT), glutamic acid-pyruvic acid transaminase (GPT), and γ-glutamyl transpeptidase (γ-GTP).

DETAILED DESCRIPTION OF THE INVENTION

Figure 1:
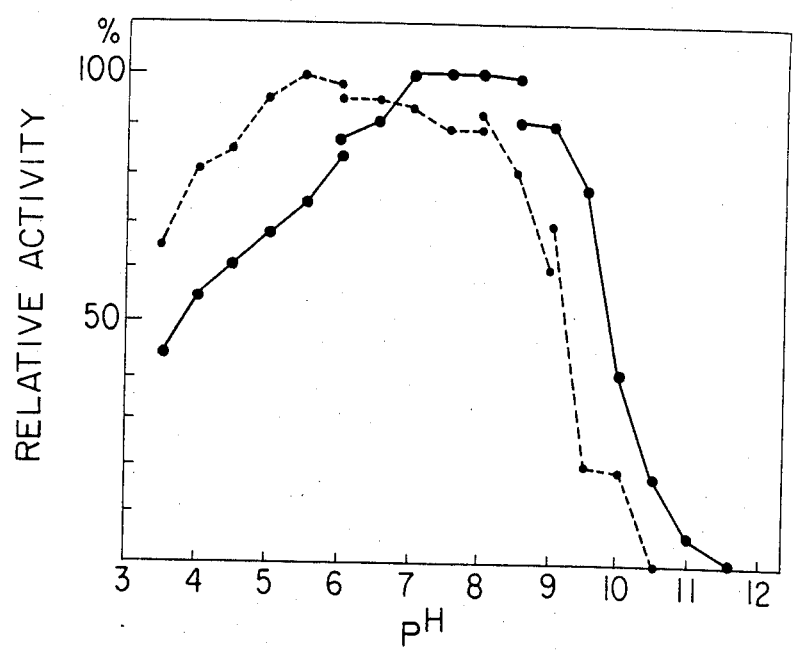
FIG. 1 is a graph showing active pH ranges of the novel enzyme (solid line) and the known enzyme (broken line)

[I] Novel enzyme:

The novel enzyme may be any L-glutamic acid oxidase which has a high stability and a very high substrate specificity for L-glutamic acid, substantially without action on amino acids other than L-glutamic acid, regardless of its preparation method.

An example of the novel enzyme is the enzyme obtained from the cultured product of a microorganism belonging to the genus Streptomyces, the properties and the method for preparation of this exemplary enzyme being detailed below.

(A) Enzymological and physicochemical properties of the novel enzyme

The purified enzyme sample of the L-glutamic acid oxidase prepared according to the method of Example A1 (Reference) hereinafter described has enzymological and physicochemical properties as set forth below.

(1) Action:

The novel enzyme, when employing L-glutamic acid as substrate, demands 1 mol of oxygen and 1 mol of water per 1 mol of L-glutamic acid, and forms 1 mol of α-ketoglutaric acid, 1 mol of ammonia and 1 mol of hydrogen peroxide, as shown in the following reaction scheme.

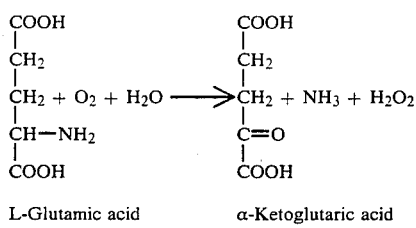

L-Glutamic acid     α-Ketoglutaric acid (2) Substrate specificity:

Table 1 shows the results obtained when the purified preparation of the novel enzyme was caused to catalyze the oxidation of various amino acids. The concentration of each substrate was 10 mM, and the reactions were carried out at pH 7.4 (0.1 M potassium phosphate buffer) and pH 6.0 (0.1 M acetate buffer). The enzyme activities were measured according to the oxygen electrode method as hereinafter described, and expressed as the relative values of activities to L-glutamic acid.

TABLE 1

| Substrate | Relative Activity (%) | |
|---|---|---|
| | pH 7.4 | pH 6.0 |
| L-Glutamic acid | 100.0 | 100.0 |
| D-Glutamic acid | <0.1 | <0.1 |
| L-Aspartic acid | 0.6 | <0.1 |

TABLE 1-continued

| Substrate | Relative Activity (%) | |
|---|---|---|
| | pH 7.4 | pH 6.0 |
| L-Glutamine | <0.1 | <0.1 |
| L-Asparagine | <0.1 | <0.1 |
| Glycine | <0.1 | <0.1 |
| L-Alanine | <0.1 | <0.1 |
| L-Valine | <0.1 | <0.1 |
| L-Leucine | <0.1 | <0.1 |
| L-Isoleucine | <0.1 | <0.1 |
| L-Serine | <0 1 | <0.1 |
| L-Threonine | <0.1 | <0.1 |
| L-Phenylalanine | <0.1 | <0.1 |
| L-Tyrosine | <0.1 | <0.1 |
| L-Proline | <0.1 | <0.1 |
| L-Lysine | <0.1 | <0.1 |
| L-Ornithine | <0.1 | <0.1 |
| L-Histidine | <0.1 | <0.1 |
| L-Arginine | <0.1 | <0.1 |
| l-Cysteine | <0.1 | <0.1 |
| L-Methionine | <0.1 | <0.1 |

As described above, the novel enzyme has a high substrate specificity for L-glutamic acid. For other amino acids, it exhibits only a little activity (0.6%) for L-aspartic acid at pH 7.4, exhibiting substantially no activity for other L-amino acids including L-glutamine, on L-histidine and for D-glutamic acid. It exhibits substantially no activity even for L-aspartic acid at pH 6.0.

As contrasted to the novel enzyme, the known enzyme as described above exhibits no activity for L-aspartic acid (0.1% or less), but exhibits activities of 8.4% for L-glutamine and 6.8% for L-histidine, respectively. Thus, both enzymes are different from each other in substrate specificity.

The novel enzymes has a km value for L-glutamic acid of $2.1 \times 10^{-4}$ M at pH 7.4, and a km value for L-aspartic acid of $2.9 \times 10^{-2}$ M at pH 7.4.

(3) Assay of activity:

The activity of the novel enzyme was assayed according to the oxygen electrode method. That is, 1 ml of 0.1 M potassium phosphate buffer (pH 7.4) containing 10 mM sodium L-glutamate was charged into an oxygen electrode cell and 10 μl of an enzyme solution was added thereto to measure the oxygen consumption rate. One unit of enzyme was determined as the amount of enzyme which consumes 1μ mol of oxygen per minute at 30° C. in the absence of catalase (unit: hereinafter abbreviated as "U").

Since the dissolved oxygen concentration is reduced with elevation of the temperature, the above method cannot be used for activity assay at higher reaction temperatures. In such a case, the activity assay is conducted according to the MBTH method [Anal. Biochem., 25, 228 (1968)]. That is, a reaction mixture containing sodium L-glutamate, catalase and the novel enzyme is incubated at an appropriate temperature for 20 minutes and the reaction is terminated with addition of trichloroacetic acid (TCA). To the terminated reaction mixture are added an acetate buffer (pH 5.0) and 3-methyl-2-benzothiazolinonehydrazone hydrochloride (MBTH) for incubation at 50° C. for 30 minutes, followed by cooling to room temperature, and thereafter the absorbance at 316 nm is measured to determine quantitatively the α-ketoglutaric acid formed from a calibration curve.

(4) Optimum pH:

The optimum pH is around pH 7 to 8.5 as shown in FIG. 1. The enzyme activities at respective pH values were assayed at 30° C. by using sodium L-glutamate as a substrate in 0.2 M acetate buffer (pH 3.5–6.0), 0.2 M potassium phosphate buffer (pH 6.0–8.5) and 0.2 M glycine-sodium chloride-sodium hydroxide buffer (pH 8.5–12.0).

In FIG. 1, for the purpose of comparison with respect to the optimum pH between the novel enzyme and the known enzyme, both of the pH activity curves of the novel enzyme (solid line) and the known enzyme (broken line: reference is made to FIG. 1 in Japanese Patent Laid-Open Publication No. 43685/1982) are shown.

As is apparent from FIG. 1, the novel enzyme is different from the known enzyme also in the optimum pH.

Also, when employing aspartic acid as the substrate, the acting pH range is narrow, the optimum pH being 7 to 8, and the enzyme has substantially no action on L-aspartic acid at pH of 6.0 or less or at pH 10.0 or more (at pH 6.0, 0.1% or less of the relative activity for glutamic acid).

(5) pH stability:

After maintaining the enzyme at respective pH values of from pH 3.5 to 11.5, under the conditions of 37° C. for 60 minutes, 45° C. for 15 minutes and 60° C. for 15 minutes, the enzyme activity for glutamic acid was assayed at pH 7.4.

Figure 3:
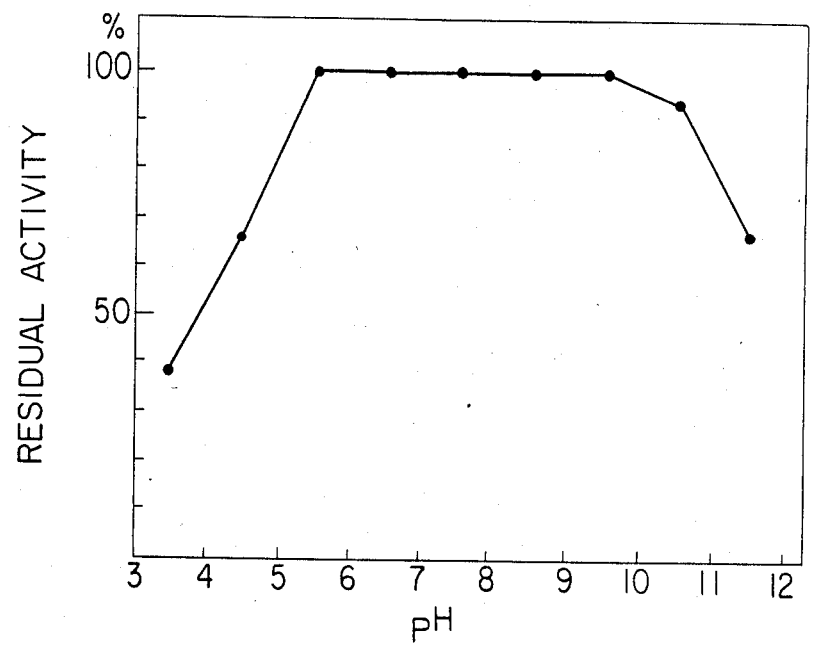
FIG. 3 is a graph showing the stable pH range (45° C., maintained for 15 minutes) of the novel enzyme.
Figure 4:
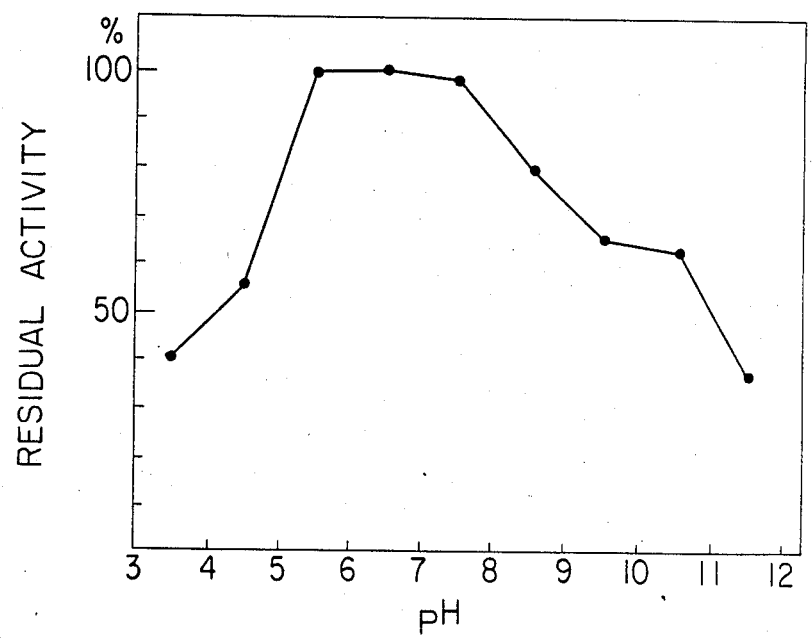
FIG. 4 is a graph showing the stable pH range (60° C., maintained for 15 minutes) of the novel enzyme.

As a result, under the conditions of 37° C. for 60 minutes, the enzyme was stable at a pH range from 5.5 to 10.5 (FIG. 2, solid line); stable at a pH range from 5.5 to 9.5 under the conditions of 45° C. for 15 minutes (FIG. 3); and stable at a pH range from 5.5 to 7.5 under the conditions of 60° C. for 15 minutes (FIG. 4).

Figure 2:
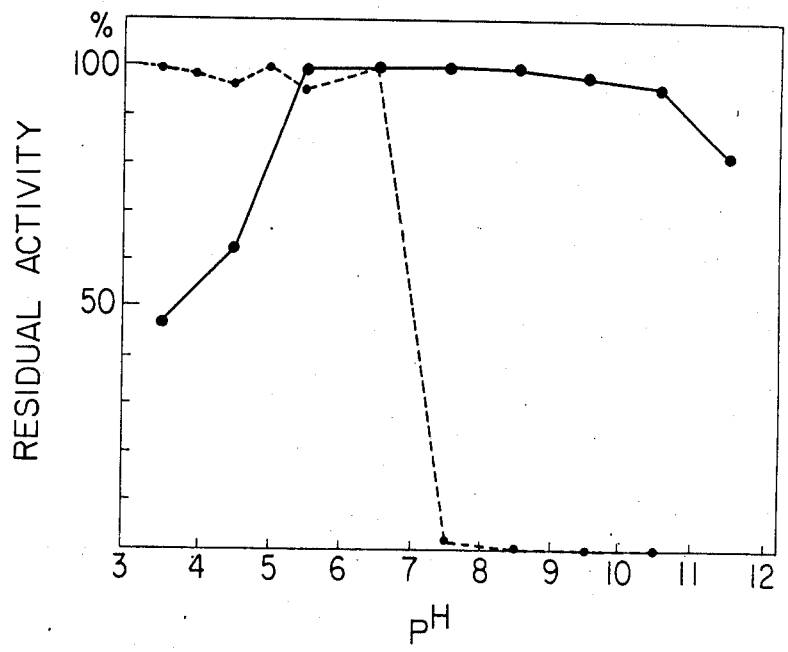
FIG. 2 is a graph showing stable pH ranges (37° C., maintained for 60 minutes) of the novel enzyme (solid line) and the known enzyme (broken line)

In FIG. 2, for the purpose of comparison relative to pH stability between the novel enzyme and the known enzyme, both of the pH stability curves of the known enzyme (broken line: reference is made to FIG. 2 in Japanese Patent Laid-Open Publication No. 43685/1982) and the novel enzyme are shown.

As is apparent from FIGS. 2, 3, and 4, when stable pH ranges are compared between the novel enzyme and the known enzyme, both are clearly different from each other, the former being stable at a wider pH range as compared with the latter.

(6) Suitable acting temperature range:

At respective temperatures of 30° C. to 80° C., the reactions were carried out for 20 minutes with the use of sodium L-glutamate as a substrate, and the enzyme activity was assayed according to the MBTH method as described above.

Figure 5:
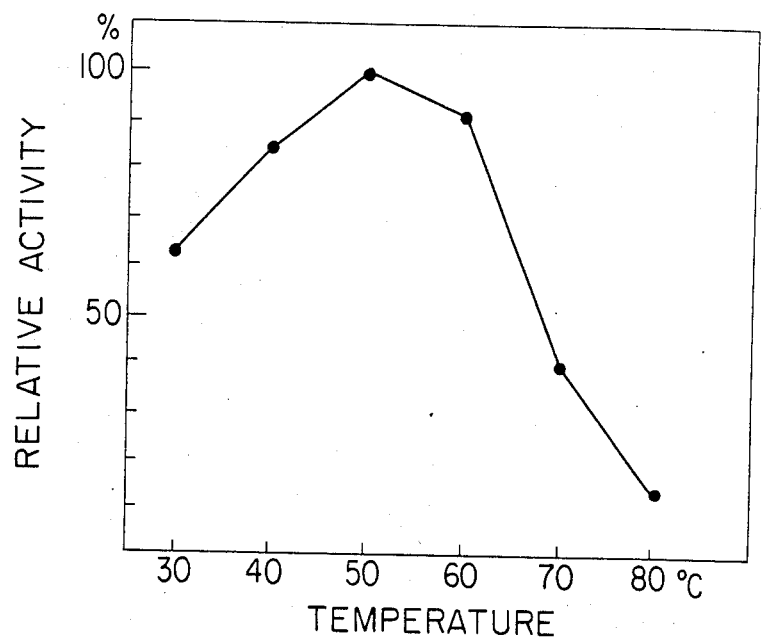
FIG. 5 is a graph showing the optimum acting temperature range of the novel enzyme.

As a result, the suitable acting temperature range of the novel enzyme was found to be 30° to 60° C., with the optimum acting temperature being around 50° C. (FIG. 5).

(7) Thermal stability:

After maintaining the enzyme at respective temperatures of 40° C. to 90° C. under the respective conditions of pH 5.5, pH 7.5 and pH 9.5, for 15 minutes, the enzyme activity for glutamic acid was assayed at pH 7.4.

Figure 6:
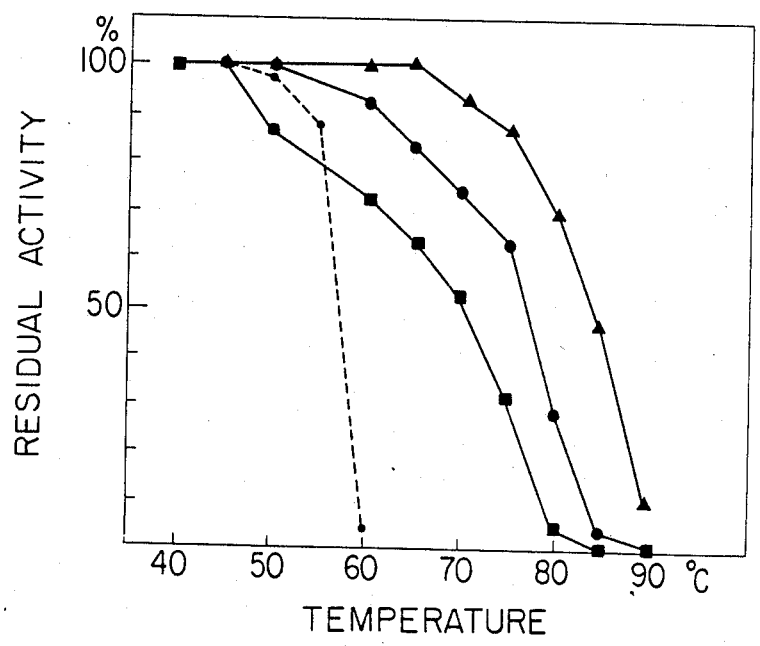
FIG. 6 is a graph showing stable temperature ranges of the novel enzyme for different pH values (solid line) and the known enzyme (broken line)

As a result, the enzyme was found at pH 5.5 to be stable up to 65° C., exhibiting a residual activity of about 50% at 85° C. (FIG. 6, ▲—▲). At pH 7.5, it was stable up to 50° C., exhibiting a residual activity of about 60% at 75° C. (FIG. 6, ●—●). At pH 9.5, it was stable up to 45° C., exhibiting a residual activity of about 50% at 70° C. (FIG. 6, ■—■).

For the purpose of comparison with regard to thermal stability between the novel enzyme and the known enzyme, the temperature stability curve of the known enzyme (broken line: reference is made to FIG. 3 in Japanese Patent Laid-Open Publication No. 43685/1982) and that of the enzyme of the present invention are shown in the same drawing.

As is apparent from FIG. 6, the novel enzyme has a higher thermal stability than the known enzyme.

(8) Inhibition, Activation and Stabilization:

For examination of the effects of various additives on the activity of the novel enzyme, enzymatic reaction was carried out in a reaction mixture (pH 7.4) containing each of the substances shown in Table 2 at a concentration of 1 mM.

The results are as shown in Table 2.

TABLE 2

| Additives | Relative activity | Additives | Relative activity |
|---|---|---|---|
| (No addition) | 100 | MnSO$_4$ | 102.1 |
| KCl | 111.1 | CoSO$_4$ | 100.7 |
| NaCl | 95.8 | Al$_2$(SO$_4$)$_3$ | 93.8 |
| KI | 100.7 | EDTA[1] | 96.5 |
| NaF | 107.6 | NEM[2] | 94.4 |
| CaCl$_2$ | 100.0 | PCMB[3] | 55.6 |
| CuCl$_2$ | 100.7 | o-phenanthroline | 97.8 |
| BaCl$_2$ | 95.1 | α,α'-dipyridyl | 94.4 |
| NiCl$_2$ | 96.5 | NaN$_3$ | 100.6 |
| StCl$_2$ | 97.2 | DDTC[4] | 100.7 |
| Li$_2$SO$_4$ | 93.8 | Tiron[5] | 100.7 |
| ZnSO$_4$ | 90.3 | (trade marK) | |

[1]EDTA: ethylenediaminetetraacetic acid
[2]NEM: N—ethylmaleimide
[3]PCMB: p-chloromercuribenzoate
[4]DDTC: diethyldithiocarbamate
[5]Tiron: 4,5-dihydroxy-1,3-benzenedisulfonic acid disodium salt As is apparent from Table 2, the activity of the novel enzyme is inhibited by about 45% by p-chloromercuribenzoate but is not inhibited at all by cupric chloride and diethyldithiocarbamate. On the other hand, the activity of the known enzyme is completely inhibited by cupric chloride and diethyldithiocarbamate. Therefore, both of the enzymes are different from each other also with respect to the effect by inhibitors.

At present, no activator and stabilizer have been found for the novel enzyme.

Figure 7:
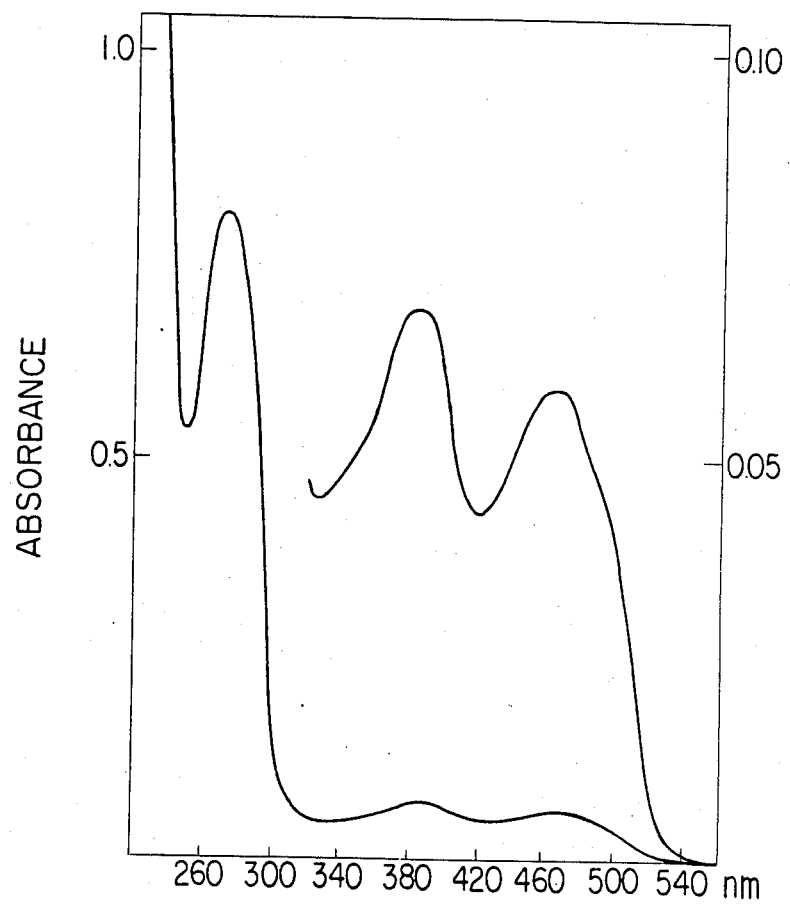
FIG. 7 is a graph showing the UV-absorption spectrum of the novel enzyme.

(9) UV-absorption spectrum (see FIG. 7):

$\lambda_{max}$: 273 nm, 385 nm, 465 nm

Shoulder: around 290 nm, around 490 nm

(10) Coenzyme:

The absorption spectrum of the supernatant obtained by heat treatment or trichloroacetic acid (TCA) treatment of the novel enzyme was identical with that of flavin adenine dinucleotide (FAD). The supernatant activated the apoenzyme of D-amino acid oxidase, and therefore the coenzyme of the novel enzyme was found to be FAD.

The yellow compound in the supernatant was also identified as FAD from the Rf value in thin layer chromatography.

FAD was estimated to exist in an amount of 2 mol per 1 mol of the novel enzyme.

(11) Polyacrylamide gel electrophoresis:

The purified novel enzyme exhibited a single band.

(12) Molecular weight:

The novel enzyme was estimated to have a molecular weight of 135,000±10,000 according to the gel filtration method by the use of Sephadex G-200 (produced by Pharmacia Fine Chemicals, Inc.).

(13) Isoelectric point:

The isoelectric point was measured by electrophoresis by the use of Ampholine (produced by LKB Co.) to find that PI was 6.2.

(14) Crystalline structure and elemental analysis:

The novel enzyme was not crystallized, and no measurement has been performed.

(15) Purification method:

The novel enzyme can be purified according to procedures involving salting out, isoelectric point precipitation, precipitation by an organic solvent, adsorption with diatomaceous earth, activated charcoal, etc., various chromatographies, and others. Examples of the purification methods are shown in Example A1 (Reference).

(B) Preparation of the novel enzyme

The method for producing the novel enzyme will now be described in detail.

Microorganism employed

The microorganism employed in the production of the novel enzyme belongs to the genus of Streptomyces and is a microorganism capable of producing the enzyme.

Illustrative of such a microorganism is the X-119-6 strain isolated as a single strain from a soil sample in Tōnoshō-machi, Katori-gun, Chiba-ken, Japan. The properties of this strain are described below.

A. Microscopic observation:

Aerial mycelia are straight with widths of 0.9 to 1.0$\mu$, exhibiting simple branching. Sporophores consist of a number of chains of spores, forming spirals of 2 to 5 rotations. Spores are somewhat ellipsoidal with sizes of 0.9–1.0×1.1×1.2$\mu$, and the surface is observed by electron microscope to have a spiny structure. No breaking of the basal mycelia is observed.

B. Observation by naked eye:

The results of observation by naked eye after growth on various media (30° C., 16 days' cultivation) are as follows.

(1) Sucrose-nitrate agar medium:

Its growth is poor. The basal mycelia are grayish brown and do not penetrate into the agar, and the aerial mycelia are powdery and spread radially on the agar. The aerial mycelia are grayish brown, with formation of gray spores. No formation of pigment into the medium is observed.

(2) Glucose-asparagine agar medium:

Its growth is good. The basal mycelia are white yellow, penetrate into the agar, and are also slightly raised. The aerial mycelia are white with no formation of pigment into the medium.

(3) Glycerin-asparagine agar medium:

Its growth is good. The basal mycelia are white yellow, penetrate into the agar, and are also raised. No aerial mycelium is formed, and no formation of pigment into the medium is observed.

(4) Starch-inorganic salts agar medium:

Its growth is good. The basal mycelia are white yellow, penetrate into the agar, and are also raised. The aerial mycelia are white and abundant with formation of gray spores. No pigment formation into the medium is observed.

(5) Tyrosine-agar medium:

Its growth is good. The basal mycelia are white yellow. The aerial mycelia are white and abundant with formation of gray spores. No pigment formation into the medium is observed.

(6) Nutrient-agar medium:

Its growth is very good. The basal mycelia are white yellow, penetrate into the agar, and are also raised. The aerial mycelia are white, with no formation of spore being observed. No pigment formation into the medium is observed.

(7) Yeast-malt agar medium:

Its growth is very good. The basal mycelia are white yellow, penetrate into the agar, and are also raised. The aerial mycelia are white and abundant with formation of gray spores. No pigment formation into the medium is observed.

(8) Oatmeal-agar medium:

Its growth is very good. The basal mycelia are white, penetrate into the agar, but are not raised on the medium. The aerial mycelia are white and abundant with formation of gray spores. No pigment formation into the medium is observed.

C. Physiological properties:

Growth temperature range is 8 to 40° C., the optimum temperature being around 35° C.

In both of the tyrosine-agar medium and the peptone-yeast-iron-agar medium, no melanin-like pigment is formed; gelatin is slightly liquefied; and starch is hydrolyzed.

D. Assimilability of various carbon sources:

Utilizations of various carbon sources on the Pridham-Gottrieb agar medium are as shown in Table 3.

TABLE 3

| Carbon source | Utilization* |
|---|---|
| D-Glucose | + |
| D-Xylose | − |
| L-Arabinose | + |
| L-Rhamnose | − |
| D-Fructose | + |
| Raffinose | + |
| Mannitol | + |
| Inositol | + |
| Sucrose | + |

*+: utilized, −: not utilized.

The above properties may be summarized as follows. That is, aerial mycelia are spiral, the surfaces of the spores being spiny. Growth on media exhibits white yellow color or grayish brown color, aerial mycelia being colored white to grayish brown, and no formation of soluble pigment and melanin-like pigment is observed. Furthermore, starch hydrolyzability is rather strong.

On the basis of these results and assimilability of carbon sources shown in Table 3, the present microorganism strain was classified according to the taxonomic system in Bergey's Manual of Determinative Bacteriology, eighth edition (1974), whereby it was found that the present microorganism strain belongs to the genus Streptomyces, but no known species sufficiently coinciding in characteristics with the present strain was found, and hence the present strain was identified to be a new microorganism strain and named Streptomyces sp. X-119-6.

The present microorganism strain was deposited at the Fermentation Research Institute, Agency of Industrial Science and Technology (FRI), 1-3, Higashi 1-chome, Yatabe-machi, Tsukuba-gun, Ibaraki-ken, Japan on June 5, 1982, and given the deposition number FERM P-6560. This strain was delivered directly from FRI to American Type Culture Collection, 12301 Parklawn Drive, Rockville, Md., U.S.A. and acquired the deposition number ATCC 39343 on Apr. 26, 1983.

The above microorganism strain is one example of the microorganism strains having high capability of producing the novel enzyme, and the microorganism to be used in the present invention is not limited thereto. It is also possible to suitably use any of the mutant strains highly capable of producing the novel enzyme obtained by subjecting the microorganism producing the enzyme to conventional microorganism mutating methods such as physical treatment by UV-ray, X-ray or γ-ray irradiation, chemical treatments with reagents such as nitrosoguanidine, etc. Further, the methods for the enzyme production are based on the function of the synthesis of the enzyme protein by the structure and regulator DNA gene in the aforesaid microorganism producing the novel enzyme. Accordingly, also included within the scope of the present invention is the production method using a microorganism, which is obtained by gene manipulation procedure, for example, by incorporating such a gene DNA into an appropriate vector which is in turn transferred by way of transformation into a microorganism belonging to a genus other than the aforesaid genus, or by permitting the gene DNA to be taken up in a microorganism belonging to the other genus by cell fusion according to the protoplast method.

Cultural method and conditions

The cultural method and conditions for cultivaing the above microorganism to be used in the present invention are not particularly limited, as long as the microorganism can sufficiently grow and the novel enzyme can be sufficiently produced, but it is preferred to use a solid cultivation method or similar method.

The solid medium to be used in solid cultivation is not different in any way from those conventionally used. That is, the solid medium is mainly composed of one kind or more kinds of natural solid materials such as wheat bran, defatted soy bean, rice bran, corn, rapeseed dregs, wheat, rice, rice hulls, etc., further containing, if desired, nutrient sources assimilable by the microorganism employed in the present invention, as exemplified by carbon sources such as glucose, sucrose, arabinose, fructose, mannitol, inositol, soluble starch, ethanol, etc., nitrogen sources such as various amino acids, peptone, soybean powders, protein hydrolysates, corn steep liquor, meat extract, yeast extract, various ammonium salts, various nitrates, urea, etc., growth promoters exemplified by salts such as various sodium salts, potassium salts, calcium salts, manganese salts, magnesium salts, zinc salts, iron salts, phosphates, sulfates, etc., and vitamins such as thiamine, riboflavin, nicotinic acid, pantothenic acid, biotin, p-aminobenzoic acid, cyanocobalamin, etc. These media may also be granulated in suitable formulations, sizes and shapes. Such a solid medium may be sterilized or denatured according to conventional procedures and then inoculated with a seed microorganism to carry out solid cultivation.

It is also possible to employ a cultivation method other than the above method, as long as the microorganism employed can proliferate and produce the novel enzyme wall, such as the method in which a liquid medium is absorbed into or coated over a suitable carrier such as sponge, etc. (see Japanese Patent Laid-Open Publication No. 14679/1974), and a seed microorganism is inoculated into the medium to be cultured therein.

The cultural conditions are not particularly limited and may be selected for optimal production of the enzyme depending on the kind of the microorganism employed. Generally, cultivation may be conducted under the conditions of, for example, 20°–30° C., pH 5–7 and 5–15 days.

Collection of the novel enzyme

The novel enzyme produced by cultivation of the microorganism employed may be separated by extraction from the cultured product, namely, the medium and/or the cultured microorganism cells, according to a suitable extraction method. The enzyme may be used as the crude enzyme solution or purified according to a conventional enzyme purification method to a purification degree which depends on the purpose of use.

The extraction method is not particularly limited but may be a conventional method. For example, extraction from the solid cultured product is ordinarily conducted with water or a buffer. The novel enzyme in microorganism cells is extracted after crushing the microorganism cells in a conventional manner and solubilizing the enzyme.

[II] Analysis of L-glutamic acid:
(1) Sample to be analyzed

The term "sample to be analyzed" used in the present description means (A) a sample which contains or is expected to contain L-glutamic acid and in which the L-glutamic acid content or its presence or absence is to be analyzed, or (B) a sample containing a reaction system which liberates or is expected to liberate L-glutamic acid, on an enzyme activity participating in the system, and the content of a substance converted to L-glutamic acid or the presence or absence of these substances is to be analyzed by measurement of the change in the L-glutamic acid content in the system.

Examples of samples classified into the above (A) are foods (e.g., liquid seasoning foods such as soy sauce, amino acid seasoning, various extracts, liquid essence of soup stock, etc.; alcohol-containing foods such as *sake*, sweet *sake*, etc.; extracts from solid foods such as fish pastes, sausages, hams, etc.), and biological samples (urine, blood, etc.). On the other hand, examples of samples classified into (B) are systems containing an enzyme producing L-glutamic acid as the reaction product such as glutaminase, glutamic acid racemase, GOT, GPT, γ-GTP, etc. and substrates therefor, and systems containing the aforesaid system and one or more kinds of other enzyme systems which can be coupled with the aforesaid system.

(2) Analysis of L-glutamic acid

The method for analysis of L-glutamic acid in the present invention comprises the enzymatic reaction system of L-glutamic acid in a sample with the novel enzyme at the pH of from pH 5 to 9, particularly the enzymatic reaction system at pH 5 to 6 for L-glutamic acid in a sample in which a large amount of L-aspartic acid is present, and a detection system of an indicator substance, which is consumed or formed with progress of the reaction, for quantitative or qualitative analysis.

Enzymatic reaction

The conditions of enzymatic reaction for analysis of L-glutamic acid are as follows.

The reaction pH may be any pH at which the novel enzyme is not inactivated and can act sufficiently on L-glutamic acid. Further, if the detection system of indicator substance depends on pH, it is preferable to set an appropriate pH. Ordinarily, the enzymatic reaction is carried out at a pH of from 5 to 9. In the case when L-aspartic acid is contained in a sample in such a large amount as to have an influence on the analysis of the L-glutamic acid, the novel enzyme may act only slightly on L-aspartic acid at the optimum pH. However, even in such a sample, L-glutamic acid can be specifically analyzed by carrying out the reaction under the conditions chosen so that the enzyme has no action on the L-aspartic acid. As such conditions, the reaction condition of from pH 5 to 6 is preferred.

For the purpose of maintaining the pH of the enzymatic reaction in a desirable range, it is preferable to use various buffers as the reaction medium. Any buffer which can maintain the aforesaid pH range, does not inhibit the activity of the novel enzyme, and has no influence on the detection system of indicator substance can be used. For example, illustrative of such buffers are phosphate buffer, Tris-hydrochloride buffer, acetate buffer, citrate buffer, and Belonal buffer.

The reaction temperature is not particularly limited. Those skilled in the art can easily determine the reaction temperature by considering the optimum temperature and stable temperature for the novel enzyme, and the detection system of indicator substance employed.

It is possible in carrying out the reaction to use the novel enzyme as a soluble enzyme or an immobilized enzyme prepared according to the methods practiced in general such as the inclusion method (the lattice type, the microcapsule type, etc.), the carrier binding method (e.g., the covalent bonding method, the ion bonding method, or the physical adsorption method), and the cross-linking method.

The modes of immobilization are not limited (see "Immobilized Enzyme", edited by Ichiro Chihata, published on Mar. 20, 1975, by Kodansha Co., Ltd.). Examples of materials suitable for the carrier or the support are cellulose (e.g., Cellophane, filter papers), cellulose derivatives including acetyl cellulose derivatives, nitrocellulose (e.g., collodion), various ion-exchange cellulose derivatives (e.g., DEAE-cellulose, TEAE-cellulose, ECTEOLA-cellulose, CM-cellulose, P-cellulose), polysaccharides such as starch, dextran derivatives [e.g., Sephadex (trade name)], agarose, mannan (e.g., konjak mannan), chitosan, carageenan, alginic acid, xanthan gum, and agar, proteins such as collagen, gelatin, fibroin, keratin, albumin, and gluten, polymeric gels such as polyacrylamide, polyvinyl pyrrolidone, and polyvinyl alcohol, synthetic organic polymers such as polyvinyl chloride, polymethyl methacrylate, polyacrylonitrile, polystyrene, polyaminostyrene, polyethylene, polypropylene, polyurethane, polycarbonate, polyamide (e.g., nylon, polyamino acid), fluorine resins [Teflon (trade name)], silicone resins, photosensitive resins, adsorbent resins, and ion-exchange resins, inorganic materials such as glass, silica, ceramic, alumina, kaolinite, bentonite, calcium phosphate, hydroxyapatite, and activated charcoal. These materials may be used as they are or after introduction of functional groups which can react with the enzyme protein or activation of the functional groups.

According to the inclusion method, the enzyme can be captured within the lattice of the gel such as of polymeric gels, cellulose derivatives, polysaccharides or proteins. With the method, the enzyme may be coated with a semi-permeable skin membrane such as that of an organic polymeric material or cellulose derivative to make a microcapsule. In the case of the carrier binding method, immobilization can be accomplished by covalent bonding onto a suitable carrier by the diazo method, the peptide method, the alkylation method or the cross-linking method (with glutaraldehyde, hexamethylene diisocyanate, etc.), by ionic bonding onto a carrier having ion-exchange groups or by physical adsorption. Also, according to the cross-linking method, immobilization can be carried out by cross-linking between enzymes with the use of a reagent having two or more functional groups such as glutaraldehyde, isocyanate derivatives (hexamethylene diisocyanate, toluene diisocyanate, etc.), isothiocyanate derivatives (hexamethylene diisothiocyanate, etc.), N,N'-ethylenebismaleinimide, N,N'-(1,2-phenylene)bismaleinimide, N,N'-(1,4-phenylene)bismaleinimide, and N,N'-polymethylene-bisiodoacetamide. Immobilized enzymes can also be prepared by practicing two or more of these methods in combination.

According to the methods as described above, the novel enzyme can be immobilized and prepared in any suitable form such as membrane, gel, granule, chip, powder, microcapsule, tube, fiber, hollow fiber, and vessel.

Detection system of indicator substance

The indicator substance for analysis of L-glutamic acid according to the method of the present invention includes oxygen consumed by the enzymatic reaction as well as hydrogen peroxide, ammonia, and α-ketoglutaric acid formed by the reaction.

Detection of each indicator substance may be performed according to any desired method, and the present invention is not limited in its detection method. That is, a known method is usually adopted as the detection method, but various methods to be developed in the future may also be considered to be available.

The detection methods for respective indicator substances are as follows.

(1) Detection of oxygen:

As a method for detection of oxygen consumed, there have been known manometric methods ("Course of Biochemical Experiments 5, Enzymatic Research Method (A)", pp. 35–41, published on Aug. 20, 1975, Tokyo Kagaku Dojin Co., Ltd.) and oxygen electrode method ("Measurement of Oxygen by the Electrode Method", edited by Bunji Hagiwara, published on Nov. 20, 1977, by Kodansha Co., Ltd.). Either method can be employed in the present invention.

Oxygen electrodes have basic structures employing as the acting electrode a noble metal such as platinum, gold, or iridium and as the reference electrode an electrode of silver, silver/silver chloride system, saturated calomel, lead, zinc, aluminum, etc., with an electrolyte (an alkali solution such as of potassium hydroxide, sodium hydroxide, etc.) existing between these electrodes. More specifically, composite type electrodes such as Clark type electrodes (FIG. 17) or separation type electrodes may be used. Their system may be either the polarographic system or the Galvanic cell system.

In measuring oxygen by means of an oxygen electrode, the dissolved oxygen in the enzymatic reaction mixture may be measured according to a conventional method. The measurement may also be conducted by the use of an enzyme electrode.

(2) Detection of hydrogen peroxide:

For detection of hydrogen peroxide formed, any of the electrochemical analytical method, the spectrophotometric analytical method, the fluorometric analytical method, the chemiluminescent analytical method, and others known in the art can be used.

As the electrochemical analytical method, a method can be employed which uses a hydrogen peroxide detecting type electrode with a structure similar to the above oxygen electrode. The analysis is conducted according to the measurement of current. For example, a highly suitable electrode is the Clark type hydrogen peroxide electrode which comprises an acting electrode of a noble metal such as platinum, a reference silver electrode, an electrolyte, and a hydrogen peroxide permeable diaphragm. Also, similarly as in the case of the oxygen electrode, it may be used as the enzyme electrode. In addition, as the electrochemical analysis, hydrogen peroxide can be determined with an ion electrode on the basis of reduction of iodine ion accompanied by the reaction among hydrogen peroxide, peroxidase and iodine ion. A catalyst degrading hydrogen peroxide such as molybdate can also be used as well as peroxidase. This method is preferably practiced with the use of an enzyme electrode.

As the spectrophotometric analytical method, there are (1) the peroxidase method in which a color former to be oxidized is caused to react with hydrogen peroxide in the presence of peroxidase or a substance exhibiting similar activity, and the absorbance of the color formed by the reaction is measured; (2) the catalase method in which an alcohol is caused to react with hydrogen peroxide in the presence of catalase, the aldehyde formed is led to a color forming system, and the absorbance of the color formed is measured, or an aldehyde dehydrogenase is caused to act on the aldehyde formed in the presence of NAD, and the amount of the reduced form of NAD (NADH) formed is measured; (3) the chemical method in which any of Ti(IV)/xylenol orange system, Ti(IV)/4-(2-pyridylazo)resorcinol system, V(V)/xylenol orange system, etc., is employed and (4) other methods.

In the peroxidase method of (1), the color development is an oxidation reaction of a color former alone or an oxidative condensation reaction of a color former with a coupler. In the former method, as the color former, o-dianisidine, o-tolidine, o-toluidine, o-aminophenol, 2,4-dichloroindophenol, benzidine, 3,3',5,5'-tetraalkylbenzidine (e.g. 3,3',5,5'-tetramethylbenzidine, etc.), 4-methoxy-1-naphthol, 2,2'-azino-di(3-ethylbenzothiazoline-6-sulfonic acid), guaiacum resin (guaiacol), N-(4-antipyryl)-aniline derivatives (e.g., N-(4'-antipyryl)-2-carboxyl-4-hydroxyaniline, etc.), p-hydroxyphenyl acetic acid, N,N-dimethyl-p-phenylenediamine, etc. can be used.

On the other hand, in the latter method, as the color former, 4-aminoantipyrine and 4-aminoantipyrine derivatives such as 4-aminoantipyrineamide; phenylenediamine derivatives such as 4-aminophenazone, 4-amino-N,N-dimethylaniline, p-phenylenediamine and 4-amino-N,N-diethyl-m-toluidine; 3-methyl-2-benzothiazolinone hydrazone (MBTH) can be used. As the coupler, phenol type, aniline type or toluidine type compounds such as phenol, catechol, resorcin, hydroquinone, cresol, guaiacol, pyrogallol, orcinol, p-chlorophenol, p-bromophenol, 2,4-dichlorophenol, 2,4-dibromophenol, 2,4,6-tribromophenol, aniline, N,N-dimethylaniline, N,N-diethylaniline, N-ethyl-(N-3-methylphenyl)-N-acetylenediamine, 3-acetamino-N,N-diethylaniline, N,N-diethyl-m-toluidine, N-ethyl-N-(2-hydroxy-3-sulfopropyl)-m-toluidine, N-glycyl-N-ethyl-m-toluidine, p-dimethylaminophenol, o-aminophenol, m-aminophenol, p-methylaminophenol, 2-chloro-6-methylphenol, 4-chloro-3-methylphenol, 3,5-dichloro-2-hydroxybenzene sulfonic acid; naphthol type compounds such as 4-halogeno-1-naphthol-2-sulfonic acid (e.g., 4-chloro-1-naphthol-2-sulfonic acid, etc.), 1-naphthol-2-sulfonic acid, 2-amino-5-naphthol-7-sulfonic acid, 2,4-dichloro-1-naphthol, 1-hydroxy-2-naphthoic acid, 4,5-dihydroxynaphthalene-2,7-disulfonic acid and the like; naphthylamine or derivatives thereof; quinoline type compounds such as hydroxyquinoline, aminoquinoline and the like can be used.

Examples of preferable combinations of a color former and a coupler are a combination of 4-aminoantipyrine with phenol, N,N-dimethylaniline, N,N-diethylaniline or N-diethyl-m-toluidine, and a combination of 3-methyl-2-benzothiazolinonehydrazone with N,N-dimethylaniline. The present invention is not limited to these kinds of color formers or combinations of a color former and a coupler, and any compound can be used as long as it can be quantitatively oxidized to develop color. As the peroxidase, an enzyme obtained from horseradish or sweet potato is ordinarily used, but any enzyme exhibiting peroxidase-like activity can be employed without particular limitation. Further, a catalyst exhibiting activity similar to peroxidase may also be used.

In the catalase methods of (2) with color formation, methanol is ordinarily used as alcohol. The color formation is ascribable to the reaction of formaldehyde formed with a hydrazone [e.g. 3-methyl-2-benzothiazolinonehydrazone, 4-amino-3-hydrazino-5-mercapto-1,2,4-triazole (AHMT), etc.] in the presence of an oxidizing agent (e.g., sodium periodate, potassium cyanophenolate, ferric chloride, etc.) or the reaction of formaldehyde with acetylacetone and an ammonium salt.

There are also the method in which glutathione is used and converted to the oxidized form of glutathione by hydrogen peroxide and glutathione peroxidase, which is in turn reduced by glutathione reductase in the presence of NADPH, and the quantity of NADPH oxidized is measured (Anal. Biochem. 76, 184–191, 1976), and the method in which indigo carmine is discolored by oxidation by a copper ion-histamine system and the analysis is made from reduction in its color degree.

In one example of the fluorometric methods, homovanilic acid is caused to react with hydrogen peroxide in the presence of peroxidase to form 2,2'-dihydroxy-3,3'-dimethoxybiphenyl-5,5'-diacetic acid, the fluorescent intensity of which is measured. In an analogous method, in place of homovanilic acid, p-hydroxyphenyl acetic acid, diacetylfluorescein derivatives (e.g. diacetylfluorescein, diacetyldichlorofluorescein, etc.) may also be used as the fluorescent reagent. In another method a fluorescent substance such as scopoletin, 3,5-diacetyl-1,2-dihydrolutidine, etc. is oxidized by hydrogen peroxide/peroxidase to form a non-fluorescent substance, and the degree of the reduction in the fluorescence intensity is measured.

In the chemiluminescent analytical method, luminol is caused to react with hydrogen peroxide in the presence of peroxidase, and the amount of luminescence is measured (see Japanese Patent Laid-Open Publications Nos. 71399/1982 and 71400/1982). In an analogous method, isoluminol, pyrogallol, bis(2,4,6-trichlorophenyl)oxalate, etc. may also be used in place of luminol, and hemoglobin, hematine, hemine, potassium ferricyanide (III), cobalt chloride may also be employed as the catalyst in place of peroxidase.

(3) Detection of ammonia:

Ammonia can be detected according to the micro-Kjeldahl method, the Nessler reagent method, the indophenol method, the ninhydrine method, or the phenosafranin method. Electrochemical analysis may also be possible according to the method in which ammonium ion is analyzed by a cation selective electrode or the method in which ammonia is analyzed as ammonia gas by an ammonia gas electrode comprising a glass electrode having thereon a hydrophobic gas permeable film. Further, L-glutamic acid can be analyzed by detection of ammonia by an enzyme electrode comprising a combination of these electrodes with the novel enzyme.

(4) Detection of α-ketoglutaric acid:

For detection of α-ketoglutaric acid, there can be used the method in which it is caused to react with 3-methyl-2-benzothiazolinonehydrazone (MBTH), and absorbance of the product formed is measured, the method in which it is caused to react with 2,4-dinitrophenylhydrazine, and absorbance of the product formed is measured, the method in which it is caused to react with o-phenylenediamine, and absorbance of the product formed is measured, and other known methods.

(3) Reagent for analysis

The reagent for analysis of the present invention is a reagent containing at least the novel enzyme. That is, its form is not limited and it may be a soluble enzyme in a form of solution, powder, or granule. Further, it may be an immobilized enzyme prepared by various methods on a carrier in the form of membrane, gel, granule, powder, chip, microcapsule, tube, fiber, hollow fiber, or vessel as mentioned previously. It may also incorporate, in addition to the novel enzyme, buffers such as a liquid or powdery phosphate buffer, Trishydrochloride buffer, acetate buffer, citrate buffer, Belonal buffer, etc.; salts (e.g., sodium chloride); sugars (e.g., sucrose); polyhydric alcohols (e.g., glycerol, propylene glycol, sorbitol); and other suitable stabilizers, surfactants, etc.

In the analysis of L-glutamic acid, the above reagent for analysis may be used so as to obtain the necessary enzymatic activity depending on the various detection methods as described above. It is also possible to previously seal an aliquot of the reagents corresponding in amount to the respective detection methods in a vessel such as a reagent vial or ampoule.

(4) Kit for analysis

The kit for analysis consists essentially of the above reagents for analysis and reagents for the detection of the enzymatic reaction. The reagents for detection are those necessary for measurement of the indicator substance as described above. That is, when hydrogen peroxide is used as the indicator substance, illustrative of the reagent for detection are, for example, a combination of peroxidase or a peroxidase-like active substance with a color former or a color former and a coupler, a combination of catalase or a catalase-like active substance with an alcohol and a reagent necessary for a color forming system or a reagent necessary for a coupling enzyme system, a combination of peroxidase or a peroxidase-like active substance with a fluorescence-emitting agent, and a combination of peroxidase or a peroxidase-like substance with a luminous reagent. Examples of these reagents will be apparent from the description in the foregoing "Detection of hydrogen peroxide".

Similarly, when ammonia or α-ketoglutaric acid is used as an indicator substance, a reagent necessary for detection can be combined with the reagent for analysis containing the novel enzyme to constitute a kit for analysis.

The reagent for analysis containing the novel enzyme and the aforesaid reagent for detection may be all mixed to form a single reagent, or when there exist some components interfering with each other, the respective components may be divided separately into suitable combinations. These may be prepared either as solutions or powdery reagents, or they may be incorporated in an appropriate support such as filter papers or films to prepare test papers or films for analysis.

To the kit for analysis of the present invention may also be added a standard reagent containing a certain quantity of L-glutamic acid in addition to the reagents as described above.

As a preferable example of the kit for analysis of the present invention, a kit for analysis of L-glutamic acid by spectrophotometric detection of hydrogen peroxide may be mentioned. For example, in the case of a kit according to the peroxidase method, ordinarily 0.02 U or more/test of the novel enzyme, 1 to 10 U/test of peroxidase and a suitable amount of the color former may be employed. When, as the color former, 4-aminoantipyrine and phenol or N,N-dimethylaniline are to be employed, these reagents are used in an amount of 1 mole or more, preferably 2 moles or more, per mole of hydrogen peroxide formed.

[III] Biosensor:

(1) Constitution of sensor

In the present invention, the "biosensor" means a device for analyzing the amount of a substance to be detected, in a sample, which comprises an enzyme as the receptor portion for distinguishing a substance to be detected, and a transducer portion which is a signal transducing site for detecting the chemical or physical change accompanying with enzymatic reaction. [See "Kagaku no Ryoiki (Region of Chemistry), special No. 134, Biomaterial Science Vol. 1", pp. 69-79, Apr. 20, 1982, published by Nankodo Co., Ltd.; and "Kagaku Kogyo (Chemical Industry)", Vol. 6, 1982, pp. 491-496]. As mentioned above, the biosensor employing an enzyme as the receptor portion is also called an "enzyme sensor", and particularly the enzyme sensor employing an electrochemical device as the transducer portion is also called an "enzyme electrode" (see "Ion Electrode and Enzyme Electrode", edited by Shuichi Suzuki, pp. 65-106, Nov. 1, 1981, published by Kodansha; and "Region of Chemistry", Vol. 36, No. 5, pp. 343-349, 1982). There are two types of enzyme sensor. One is the mounting type enzyme electrode in which a receptor portion is provided in contact with or adjacent to a transducer portion, and another is the reactor type enzyme sensor in which a receptor portion and a transducer portion are separated from each other.

The present invention constitutes a novel biosensor using a specific L-glutamic acid oxidase which is a novel enzyme as the receptor portion as mentioned above, whereby it has attained an effectiveness superior by far to that of the prior art technique. Accordingly, the known techniques can be used in the present invention except for the use of the novel enzyme, and, further, the techniques to be developed in the future can also be employed as long as they are suited for the purpose of the present invention.

(2) Receptor portion

In order to use the novel enzyme as the receptor portion of the biosensor, the receptor portion must be constituted to make good contact and reaction of the enzyme with L-glutamic acid in a sample. To prevent a leak of the enzyme from the receptor portion, the enzyme is ordinarily immobilized or adsorbed on a semipermeable membrane (e.g., dialyzing membrane or ultrafiltration membrane) before it is provided for use.

Immobilization may be performed according to any method suitable for the purpose of use of the receptor portion in the biosensor, which is not particularly limited as long as it does not substantially inactivate the novel enzyme and interfere with the enzymatic reaction [see "Immobilized Enzyme", edited by Ichiro Chihata, Mar. 20, 1975, published by Kodansha Co., Ltd. and "Ion Electrode and Enzyme Electrode" (ibid.), pp. 65–77].

That is, in the preparation of immobilized enzyme used as the receptor portion, the immobilization method may be suitably chosen from the known methods such as the inclusion method (the lattice type, the microcapsule type, etc.), the carrier binding method (e.g., the covalent bonding method, the ion bonding method, or the physical adsorption method) and the cross-linking method. Examples of materials suitable for the carrier or the support as well as the details of each of the immobilization methods are as previously mentioned.

The immobilized enzyme obtained may be used as the receptor portion of the biosensor in the following modes. That is, in the case of the mounting type enzyme electrode, the immobilized enzyme preparation ordinarily in a form of membrane, gel, powder or microcapsule is placed on a permeable membrane which is in contact with the surface of an electrode. Then the enzyme and electrode are covered with a substrate-permeable porous membrane (e.g., dialyzing membrane, ultrafiltration membrane). The three constitutents described above, i.e. a permeable membrane, an immobilized enzyme and a covered membrane, can be constructed into a laminated membrane or a heterogeneous membrane. On the other hand, in the case of a reactor type enzyme sensor, an immobilized enzyme generally in the form of a granule or powder is packed in a column or a tube. An immobilized enzyme prepared in a form of tube, membrane, hollow fiber or fiber can also be constituted as the receptor portion to make a reactor.

(3) Transducer portion

In the aforesaid receptor portion, the substrate in a sample for analysis is oxidized by the novel enzyme and at the transducer portion the chemical or physical change by the reaction is detected and transduced into an electrical signal. In the following description, reference is made to examples in which chemical changes are detected, but a physical change such as heat balance may also be detected by means of a thermistor or the like.

The chemical changes accompanying the enzymatic reaction are consumption of oxygen and L-glutamic acid and formation of hydrogen peroxide, ammonia and α-ketoglutaric acid in the reaction mixture. The change to be detected by the transducer portion is ordinarily consumption of oxygen, formation of hydrogen peroxide or formation of ammonia.

As the transducer for detecting consumption of oxygen and transducing it into an electrical signal, an oxygen electrode may be employed.

As the transducer for detecting hydrogen peroxide and transducing the result into an electrical signal, a hydrogen peroxide detecting type electrode is employed. More specifically, it is possible to use an electrode having a structure similar to that of the oxygen electrode as described above.

Also, by using as the receptor portion a catalyst degrading hydrogen peroxide such as a peroxidase or a molybdate together with the novel enzyme, and permitting hydrogen peroxide to react with iodine ions, the activity reduction of iodine ions can be detected to determine hydrogen peroxide. In this case, an iodine ion electrode can be used.

As the transducer for detecting ammonia and transducing the result into an electrical signal, a cation selective electrode can be employed when ammonia is to be analyzed as ammonium ion, while an ammonia gas electrode can be used when ammonia is to be analyzed as ammonia gas.

The mounting type enzyme electrode according to the present invention has a structure in which the aforesaid enzyme is mounted on a membrane of various electrodes described above, or integrally combined with such a membrane.

Also, the reactor type enzyme electrode according to the present invention comprises a reactor having the immobilized enzyme as the receptor portion and an electrode described above which is remote from the site of the enzymatic reaction.

The present invention is not limited with respect to the transducer detecting substances and the transducer systems.

EXAMPLE A1 (REFERENCE)

Into an Erlenmeyer flask of 500-ml capacity were charged 20 g of wheat bran and 16 ml of water, and sterilization was conducted at 120° C. for 30 minutes. Into the wheat bran medium thus prepared, Streptomyces sp. X-119-6 (FERM P-6560, ATCC 39343) and cultured at 28° C. for 7 days to prepare seed culture.

Into each of 25 Erlenmeyer flasks of 5-liter capacity were charged 200 g of wheat bran and 160 ml of water, and after sterilization at 120° C. for 30 minutes, the above seed culture was inoculated and cultured at 28° C. for 2 days and further at 20° C. for additional 2 weeks.

The cultured product obtained was immersed in 37.5 liters of water for one hour, filtered and further passed through diatomaceous earth to obtain about 34 liters of a crude enzyme solution. Ammonium sulfate was added to the crude enzyme solution to 50% saturation, and the precipitates formed were collected by centrifugation and dissolved in 3.9 liters of 0.02M acetate buffer (pH 5.5). The reactant solution was heated at 57° C. for 30 minutes. The heat treated enzyme solution was cooled to 5° C. or lower, and then to this solution was added a two-fold amount of previously cooled ethanol. The precipitates thus formed were collected by centrifugation, dissolved in 0.02M phosphate buffer (pH 7.4), and dialyzed against the same buffer overnight.

The precipitates formed during dialysis were removed by centrifugation. The supernatant was passed through a DEAE (diethylaminoethyl)-cellulose column (3.5×50 cm) equilibrated with the same buffer, and the enzyme adsorbed was eluted with the same buffer containing 0.35M sodium chloride. The active fractions eluted were collected, and dialyzed against 0.05M acetate buffer (pH 5.5) containing 0.05M sodium chloride. The inner dialyzed solution was passed through a column (2×10 cm) of DEAE-Sepharose CL-6B (produced by Pharmacia Fine Chemicals, Inc.) equilibrated with the same buffer, and the enzyme adsorbed was eluted with 0.05–0.75M linear gradient of sodium chloride.

The active fractions eluted were collected, concentrated by dialysis, and then subjected to gel filtration by use of a Sephadex G-200 (produced by Pharmacia Fine Chemicals, Inc.) column (2.5×120 cm). The active fractions were collected and, after concentration, dialyzed against 0.02M potassium phosphate buffer (pH 7.4). The inner dialyzed solution was centrifuged, and the supernatant was subjected to microfiltration, which was followed by lyophilization to obtain 30 mg of a purified preparation of L-glutamic acid oxidase (specific activity 55.1 U/mg-protein, yield 18.4%).

EXAMPLE B1

(1) Preparation of kit:

Reagent A: In 2 ml of 0.2M potassium phosphate buffer (pH 6.5) were dissolved 1 mg of L-glutamic acid oxidase (10 U/mg), 5 mg of peroxidase (100 U/mg, obtained from horseradish, produced by Toyo Boseki Co., Ltd.) and 40 mg of 4-aminoantipyrine so as to be contained in one reagent vial. Lyophilization was then carried out according to a conventional method.

Reagent B: (1) A solution of 40 mg of phenol in 100 ml of 0.1M phosphate buffer (pH 6.5) was placed in a reagent vial or (2) a solution of 100 mg of dimethylaniline in 100 ml of 0.1M potassium phosphate buffer (pH 6.5) was placed in a reagent vial.

Figure 8:
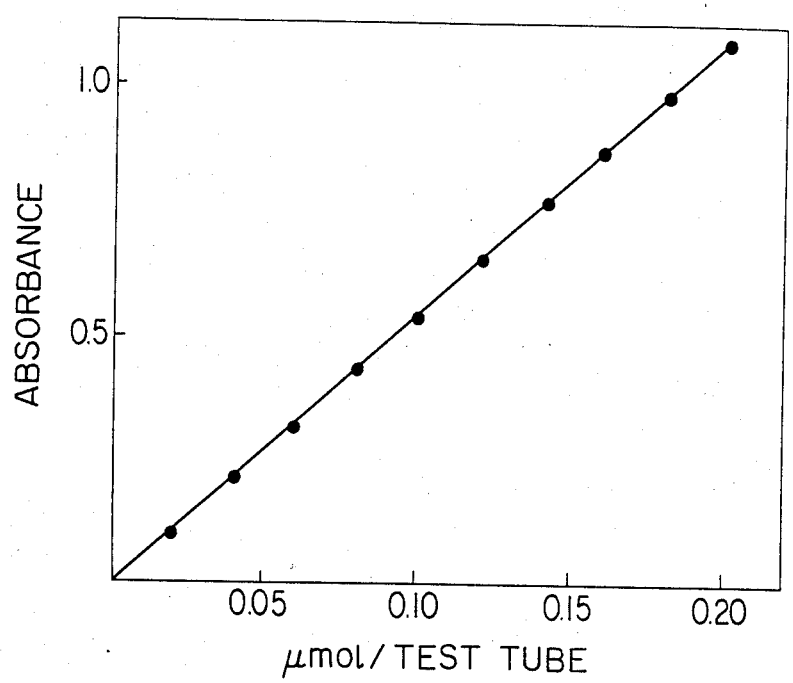
FIG. 8 and FIG. 9 are graphs respectively showing the calibration curves of L-glutamic acid when a phenol solution and a dimethylaniline solution are used as the reagent B in the kit of Example B1.
Figure 9:
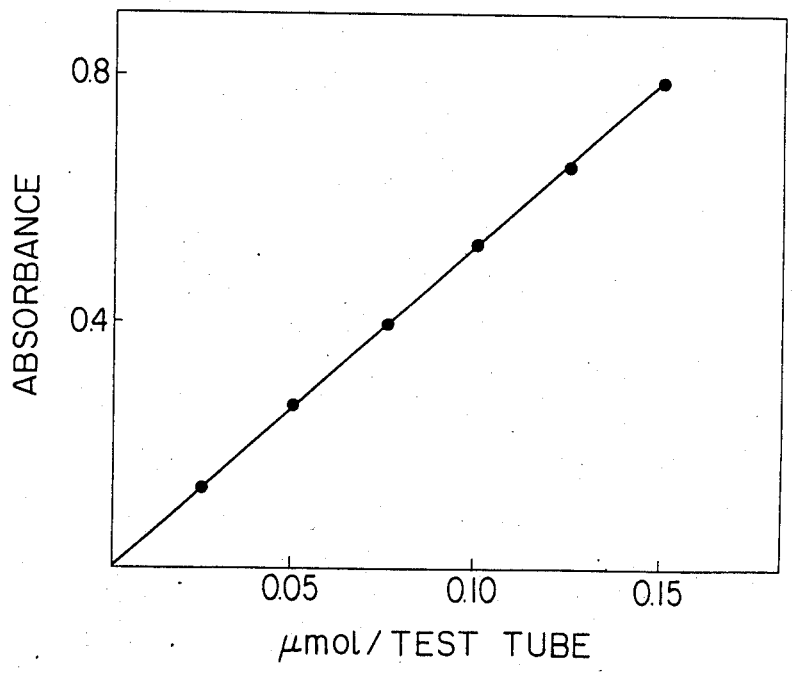

(2) Operational procedure:

In each test tube was apportioned 0.1 ml of the standard solution of sodium L-glutamate or water, and 0.9 ml of the solution prepared by dissolving the lyophilized product of the above reagent A into 100 ml of either solution (1) or (2) of the reagent B was added to each test tube. Then the incubation was carried out aerobically at 37° C. with shaking for 20 minutes. With the blind test with water as reference, the absorbance was measured at 500 nm when using the above solution (1), and at 565 nm when using the above solution (2). These calibration curves are shown in FIG. 8 (when Reagent B is (1)) and FIG. 9 (when Reagent B is (2)).

EXAMPLE B2

(1) Preparation of reagents:

Color forming reagent: In 50 ml of 0.2M potassium phosphate buffer (pH 7.4) were dissolved 20 mg of phenol, 20 mg of 4-aminoantipyrine and 3 mg of horseradish peroxidase (100 U/mg).

L-glutamic acid oxidase: In 30 ml of 0.02M potassium phosphate (pH 7.4) was dissolved 300 μg (55 U/mg) of the purified enzyme (0.55 U/ml).

Figure 10:
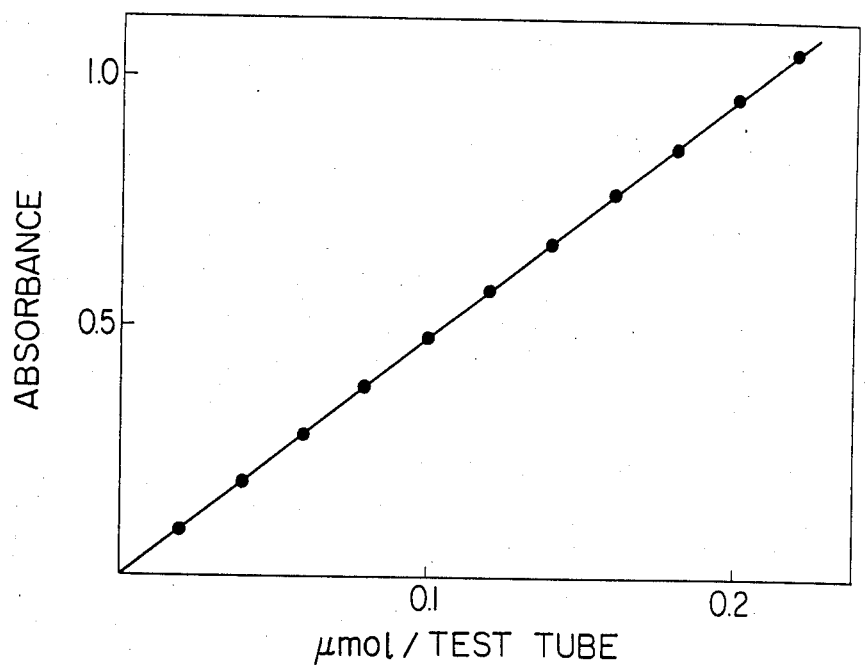
FIG. 10 is a graph showing the calibration curve of L-glutamic acid in Example B2.

(2) Operation procedure:

In each test tube was apportioned 0.8 ml of the color forming reagent, and 0.1 ml of L-glutamic acid oxidase solution was added thereto, which step was followed by preincubation at 37° C. for 5 minutes. After addition of 0.1 ml of the standard sodium L-glutamate solution (0–2 μmol/ml) or sample solution (soy sauce diluted 150-fold with water), the mixture was stirred well and incubated aerobically with shaking at 37° C. for 20 minutes. With the blind test as reference, the absorbance for the standard sodium L-glutamate at 500 nm was measured to prepare the calibration curve shown in FIG. 10. The amount of L-glutamic acid in the above samples was determined from this calibration curve as compared with the values of the amount of L-glutamic acid in the same samples according to the prior art method using an L-glutamic acid decarboxylase (the method in which color reduction degrees of phenolphthalein are measured by Technicon Autoanalyzer). The results are shown in Table 4. The correlative coefficient was $\gamma = 0.997$, the regression equation being $y = 1.005x - 0.575$.

EXAMPLE B3

Figure 11:
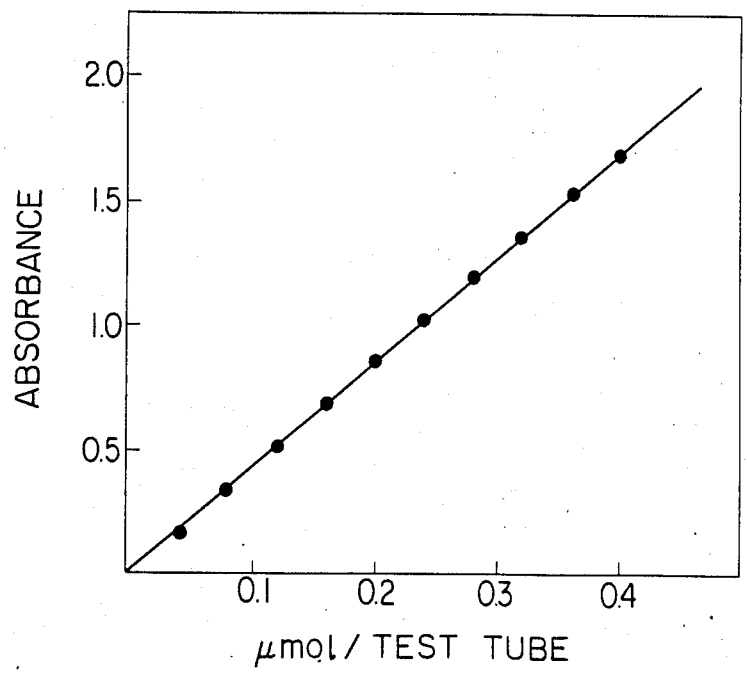
FIG. 11 is a graph showing the calibration curve of L-glutamic acid in Example B3.

In each test tube were apportioned 0.7 ml of 0.1 M potassium phosphate buffer (pH 7.4), 0.1 ml of a solution of catalase (1000 U/ml, obtained from bovine liver, produced by Sigma Chemical Co.) and 0.1 ml of a solution of L-glutamic acid oxidase (0.6 U/ml), which step was followed by preincubation at 37° C. for 5 minutes. The reaction was initiated by adding 0.1 ml of the standard sodium L-glutamate solutions (0–5 mM) or 0.1 ml of sample solutions (the same diluted solutions of soy sauce products as in Example B2). After incubation aerobically with shaking at 37° C. for 20 minutes, the reaction was terminated by addition of 0.1 ml of 25% trichloroacetic acid. To the reaction terminated mixture were added 1.9 ml of 1M acetate buffer (pH 5.0) and 0.8 ml of 0.1% 3-methyl-2-benzothiazolinonehydrazone hydrochloride solution. After stirring the mixture, the incubation was carried out at 50° C. for 30 minutes. After cooling to room temperature, with the blind test as reference, the absorbance at 316 nm was measured to prepare the calibration curve shown in FIG. 11. The amount of L-glutamic acid in the samples was determined from this calibration curve as compared with the values of the amount of L-glutamic acid in the same samples according to the prior art method using an L-glutamic acid decarboxylase. The results are shown in Table 4. The correlative coefficient was $\gamma = 0.996$, the regression equation being $y = 1.026x - 3.122$.

TABLE 4

| Samples No. | Example B2 mM | Example B3 mM | Prior art method mM |
| --- | --- | --- | --- |
| 1 | 90.0 | 94.0 | 90.7 |
| 2 | 108.5 | 105.0 | 105.7 |
| 3 | 96.0 | 96.0 | 97.2 |
| 4 | 39.0 | 39.0 | 40.7 |
| 5 | 81.0 | 81.0 | 80.0 |
| 6 | 72.0 | 69.0 | 72.2 |
| 7 | 76.5 | 72.0 | 74.3 |
| 8 | 99.0 | 94.5 | 98.6 |
| 9 | 115.5 | 117.0 | 116.4 |
| 10 | 97.5 | 100.0 | 100.0 |

EXAMPLE B4

(1) Preparation of reagents:

Color forming reagent: In 50 ml of 0.2M potassium phosphate buffer (pH 6.5) were dissolved 30 mg of phenol, 30 mg of 4-aminoantipyrine, 4 mg of horseradish peroxidase (100 U/mg) and 1 mg of L-glutamic acid oxidase (10 U/mg).

Substrate solution A: In 10 ml of 0.1M potassium phosphate buffer (pH 7.0) were dissolved 200 mg of sodium L-aspartate and 15 mg of α-ketoglutaric acid.

Substrate solution B: In 10 ml of 0.1M potassium phosphate buffer (pH 7.0) were dissoved 140 mg of L-alanine and 15 mg of α-ketoglutaric acid.

Figure 12:
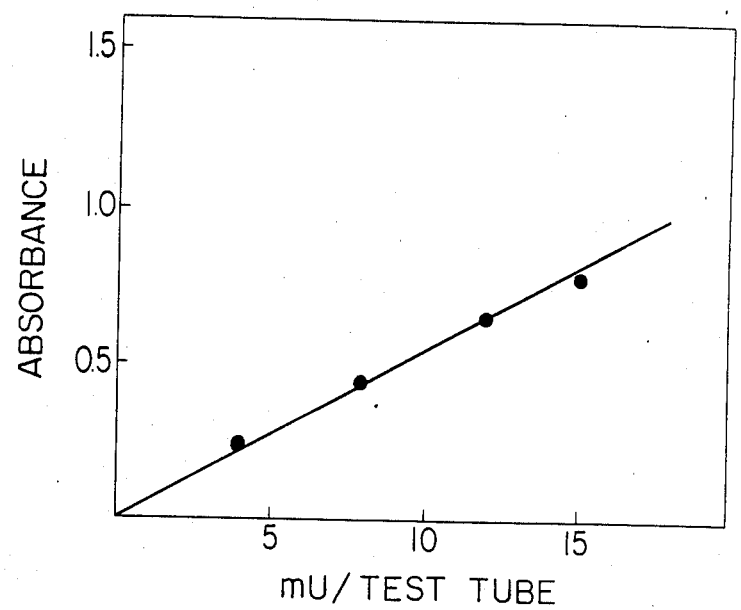
FIG. 12 is a graph showing the calibration curve of GOT activity in Example B4.

(2) Operational procedure:

(1) Assay of glutamic acid-oxaloacetic acid transaminase (GOT) activity:

In each test tube was apportioned 0.2 ml of substrate solution A, and 0.1 ml of the standard enzyme solution (Behlinger Yamanouchi Co., Ltd. 380 U/mg) wa added thereto, after which incubation was carried out 37° C. for 30 minutes, which was followed by termi tion of the reaction by addition of 0.1 ml of 25% tric roacetic acid. To the reaction terminated mixture added 0.1 ml of 1M potassium phosphate buffer (r and 0.5 ml of the color forming reagent containing L-glutamic acid oxidase, and the incubation was carried out at 37° C. for 20 minutes. With the blind test as reference, the absorbance at 500 nm was measured to prepare the calibration curve shown in FIG. 12.

Figure 13:
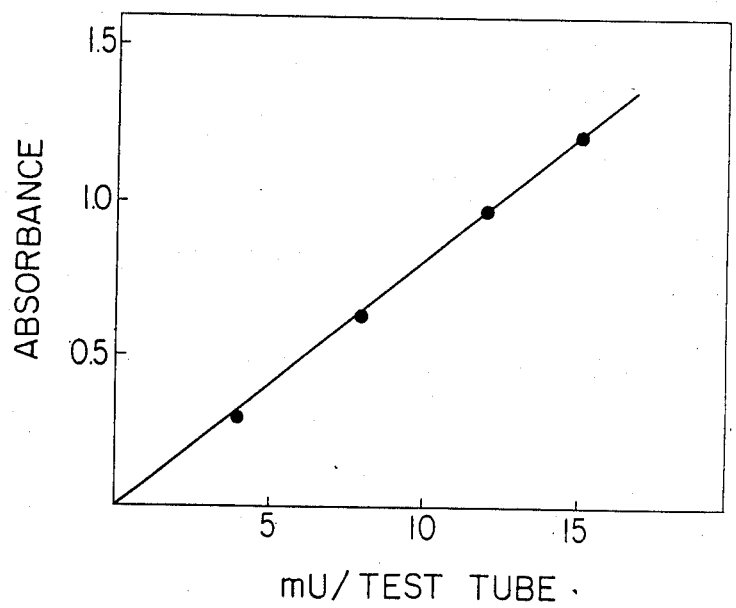
FIG. 13 is a graph showing the calibration curve of GPT activity in Example B4.

(2) Assay of glutamic acid-pyruvic acid transaminase (GPT) activity:

In each test tube was apportioned 0.2 ml of substrate solution B, and 0.1 ml of the standard enzyme solution (Behlinger Yamanouchi Co., Ltd. 140 U/mg) was added thereto, after which incubation was carried out at 37° C. for 30 minutes, which was followed by termination of the reaction by addition of 0.1 ml of 25% trichloroacetic acid. The content of L-glutamic acid in the reaction terminated mixture was measured similarly as in (1) to prepare the calibration curve shown in FIG. 13.

EXAMPLE B5

Figure 14:
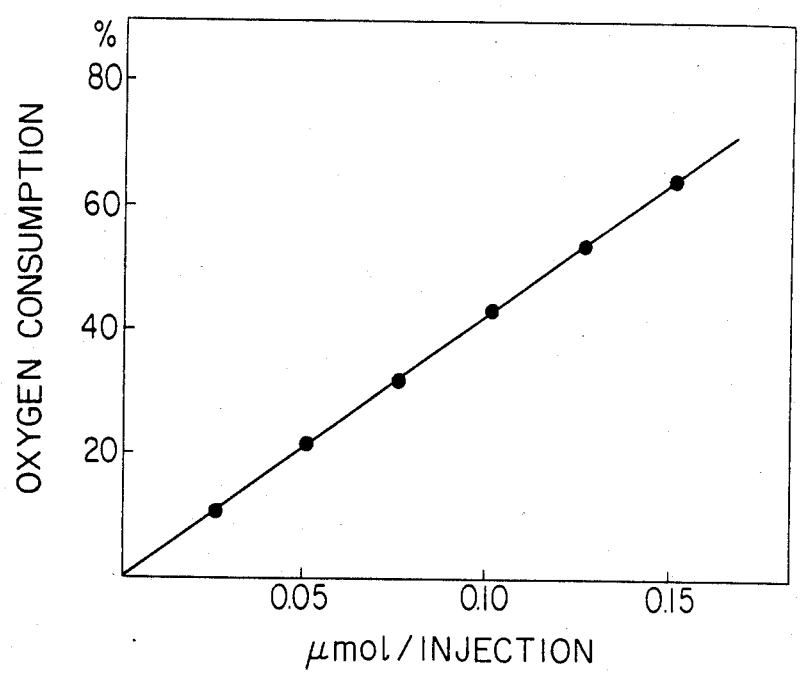
FIG. 14 is a graph showing the calibration curve of L-glutamic acid in Example B5.

One ml of 0.1M acetate buffer (pH 5.5) containing L-glutamic acid oxidase (0.5 U/ml) was sealed in the cuvette of a Clark type oxygen electorde in which thermostat water at 30° C. was circulated, and then 50 μl of L-glutamic acid standard solutions (0–2 mM) was injected thereinto for measurement of the oxygen consumed. With the results the calibration curve was prepared as shown in FIG. 14. The amount of L-glutamic acid in the samples (various products of soy sauce) was determined from this calibration curve as compared with the amount of the same samples obtained by the prior art method using an L-glutamic acid decarboxylase. The results are shown in Table 5. The correlative coefficient was $\gamma = 0.953$, the regression equation being $y = 0.930 + 6.11$.

TABLE 5

| Samples No. | Example B5 mM | Prior art method mM |
|---|---|---|
| 1 | 74.9 | 77.8 |
| 2 | 81.6 | 80.0 |
| 3 | 79.7 | 82.1 |
| 4 | 78.3 | 78.5 |
| 5 | 81.1 | 83.5 |
| 6 | 69.7 | 73.5 |
| 7 | 85.9 | 85.7 |
| 8 | 91.6 | 91.4 |
| 9 | 82.1 | 85.7 |
| 10 | 71.6 | 71.4 |
| 11 | 77.2 | 77.1 |
| 12 | 74.8 | 72.1 |
| 13 | 74.8 | 75.0 |
| 14 | 73.8 | 70.0 |
| 15 | 57.9 | 61.4 |

EXAMPLE B6

L-Glutamic acid oxidase solution (0.5 ml) (12.5 U/ml) was added dropwise under suction onto a porous nitrocellulose membrane (produced by Tōyō Kagaku Sangyō Co., Ltd.; TM-5; pore size 0.1 μm, diameter 25 mm, membrane thickness 140 μm) to be immobilized thereon by adsorption. Then an L-glutamic acid oxidase membrane was obtained after drying.

The above immobilized enzyme membrane was cut into a disc (diameter 5.0 mm), which was then mounted on the gas-permeable membrane (Teflon membrane, membrane thickness 10 μm) of a diaphragm oxygen electrode (produced by Ishikawa Seisakusho Co., Ltd., U-2Model), and further a cellulose dialyzing membrane was covered on the immobilized enzyme membrane and the electrode to prepare an L-glutamic acid sensor.

Figure 15:
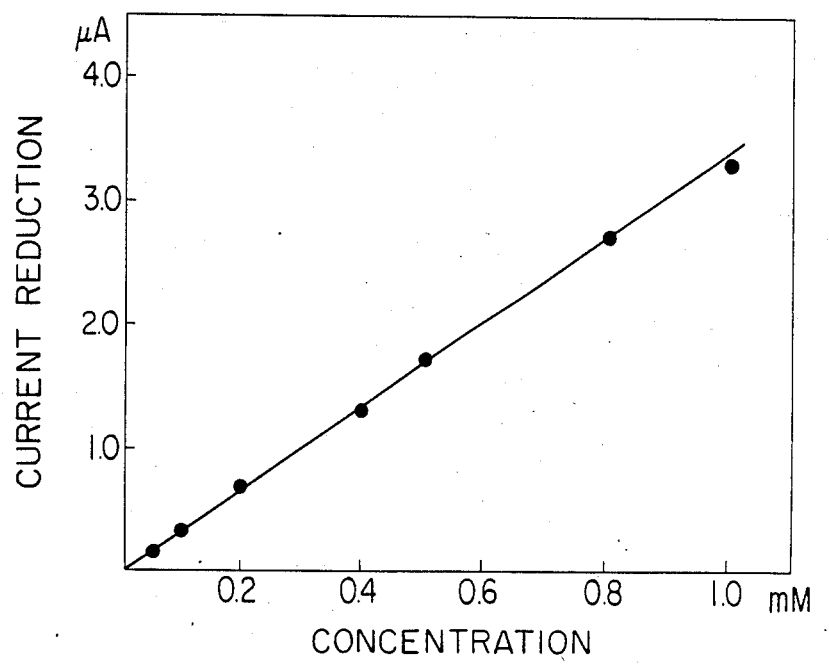
FIG. 15 is a graph showing the calibration curve of L-glutamic acid obtained by the use of the enzyme electrode of Example B6.

By the use of this sensor, current reduction value for sodium L-glutamate standard solution of known concentration (0.05–1.0 mM) was measured to prepare the calibration curve shown in FIG. 15.

EXAMPLE B7

Figure 16:
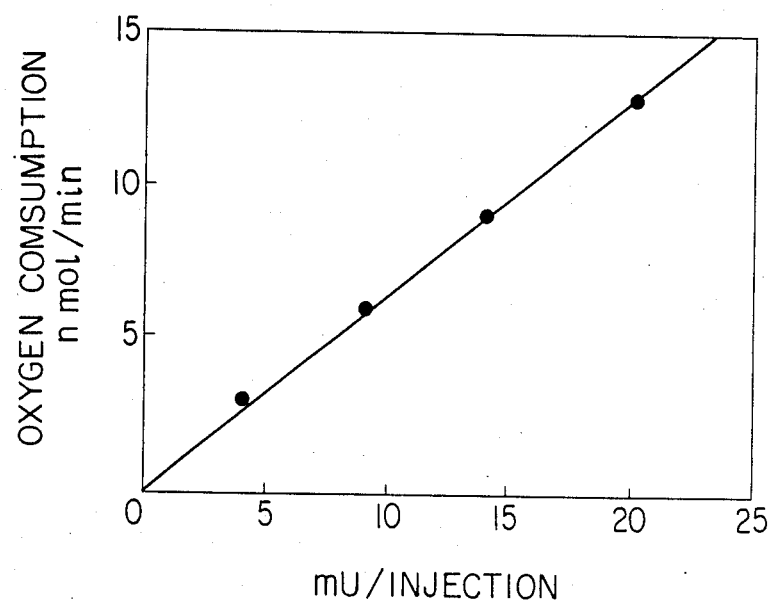
FIG. 16 is a graph showing the calibration curve of glutaminase activity in Example B7.

One ml of a 0.1M acetate buffer (pH 5.5) containing 2U of L-glutamic acid oxidase and 20 μmol of L-glutamine was sealed in the cuvette of a Clark type oxygen electrode in which thermostat water at 30° C. was circulated, and 20 μl of glutaminase standard solutions (4–20 mU, obtained from *E. coli*) was injected thereinto for measurement of the oxygen consumption rate to prepare the calibration curve shown in FIG. 16.

Similarly, 50 μl of a suspension of soy sauce *koji* (obtained by homogenizing 10 g of soy sauce *koji* in 50 ml of 0.1M phosphate buffer (pH 7.0) at 1,000 r.p.m. for five minutes and then adding the same buffer to fill up 300 ml) was injected thereinto for measurement of the oxygen consumption rate. The glutaminase activity per gram of soy sauce *koji* was found to be 3.7 U.

EXAMPLE C1

L-Glutamic acid oxidase solution (0.1 ml) (448 U/ml) was added dropwise and solidified on a Cellophane membrane (membrane thickness 30 μm, 30 mm × 30 mm square), and the resultant product was impregnated with 0.1 ml of 2.5% glutaraldehyde solution and then dried at 4° C. overnight. The membrane was washed with water until no substance absorbing at 280 nm was eluted to obtain an immobilized Cellophane membrane of L-glutamic acid oxidase.

Figure 17:
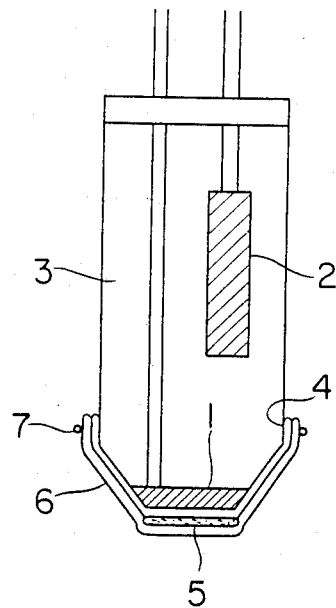
FIG. 17 is a schematic diagram showing the L-glutamic acid sensor according to the present invention.

The above immobilized enzyme membrane was cut into a piece of circular shape, which was mounted on an oxygen permeable membrane (Teflon membrane, membrane thickness 10 μm) of a diaphragm oxygen electrode (produced by Ishikawa Seisakusho Co., Ltd.), and further a cellulose dialyzing membrane (membrane thickness 50 μm, produced by Visking Co.) was covered on the immobilized enzyme membrane and the electrode to prepare an L-glutamic acid sensor (FIG. 17).

In FIG. 17, the diaphragm oxygen electrode comprises a cathode of platinum electrode 1, an anode of lead electrode 2, an internal liquid (electrolyte) 3 of a potassium hydroxide solution, and an oxygen permeable Teflon membrane 4 mounted on the platinum cathode surface. On the Teflon membrane is mounted the above immobilized enzyme membrane 5, which is further covered with a cellulose dialysis membrane 6 and fixed with an O-ring 7.

Figure 18:
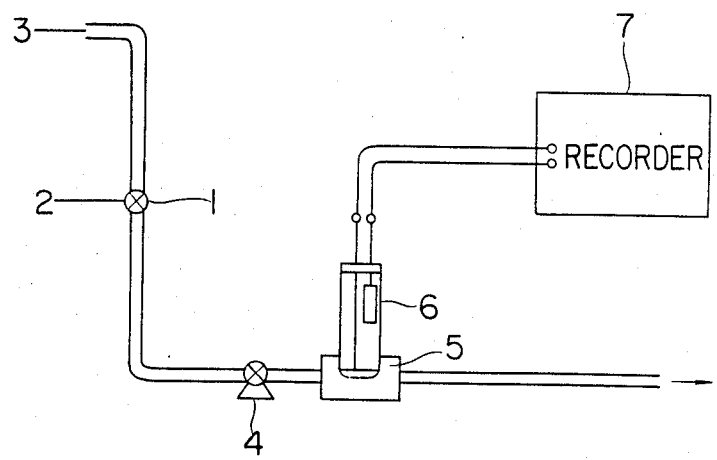
FIG. 18 is a diagram showing schematically the L-glutamic acid analyzer employing the L-glutamic acid sensor shown in FIG. 17.

By the use of the above enzyme electrode, an L-glutamic acid analyzing device as shown in FIG. 18 was prepared. In FIG. 18, the sample solution 2 injected through inlet 1 is transferred by a peristaltic pump 4 together with oxygen saturated buffer 3 into a cell 5. The current reduction value measured by the L-glutamic acid sensor 6 is recorded on the recorder 7.

Figure 19:
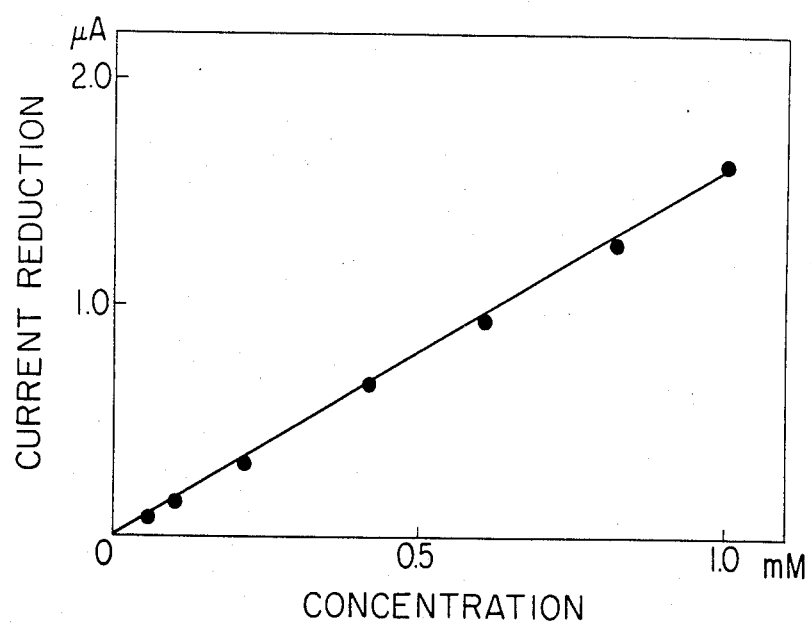
FIG. 19 is a graph showing the correlation between sodium L-glutamate concentration and the current reduction value when the device shown in FIG. 18 is used.

Sodium L-glutamate standard solution was injected into the above device for measurement of the current reduction value. The correlation between the sodium L-glutamate concentration and the current reduction was obtained as shown in FIG. 19.

Figure 20:
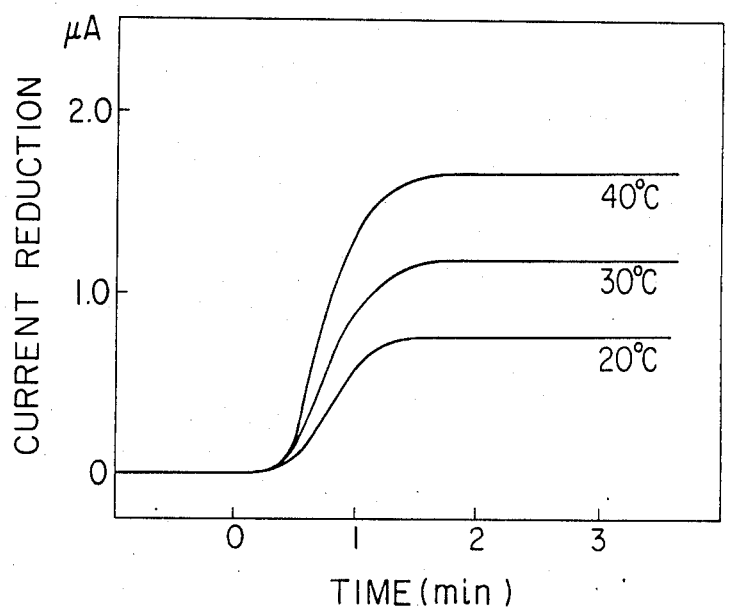
FIG. 20 is a graph showing responses at different temperatures when the device shown in FIG. 18 is used.

With the use of the device, responses at respective temperatures were measured, and the result was obtained as shown in FIG. 20. Measurements were carried out by using 0.8 mM sodium L-glutamate solutions respectively at temperatures of 20° C., 30° C. and 40° C.

Figure 21:
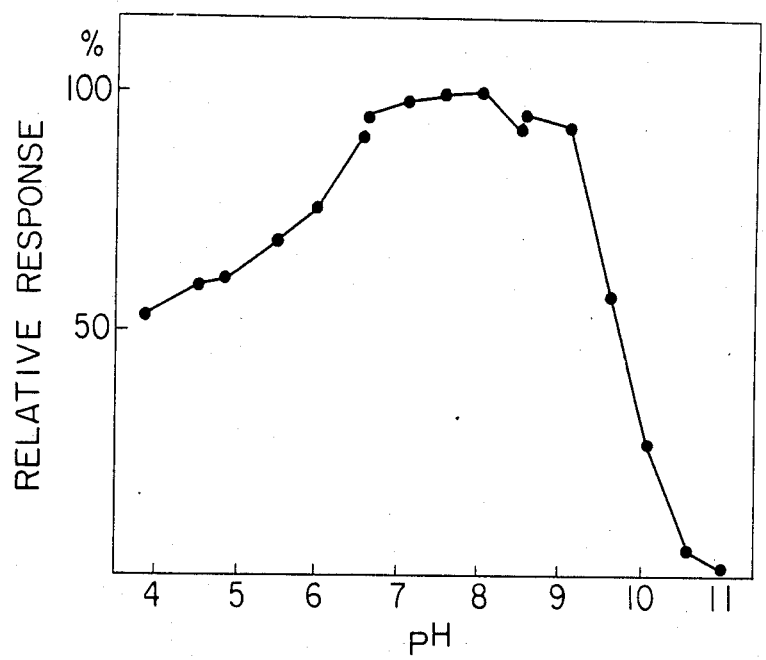
FIG. 21 is a graph showing responses at different pH values when the device shown in FIG. 18 is used.

Similarly, responses to sodium L-glutamate solution (0.8 mM) at 30° C. and different pH values were determined. The results were obtained as shown in FIG. 21.

Furthermore, responses to various amino acids were measured, and the results were obtained as shown in Table 6. In the measurement, the concentration of the solutions of amino acids other than L-glutamic acid was 2.0 mM while that of L-glutamic acid solution was 0.4 mM. The results obtained by the measurement are shown as relative responses. The reaction was carried out in 0.1M of acetic acid-sodium acetate buffer at pH 5.5 and 30° C.

TABLE 6

| Substance | Relative response (%) |
| --- | --- |
| L-Glutamic acid | 100.0 |
| D-Glutamic acid | <0.1 |
| L-Aspartic acid | <1.0 |
| L-Glutamine | <2.0 |
| L-Asparagine | <1.0 |
| Glycine | <0.1 |
| L-Alanine | <0.1 |
| L-Valine | <0.1 |
| L-Leucine | <0.1 |
| L-Isoleucine | <0.1 |
| L-Serine | <0.1 |
| L-Threonine | <0.1 |
| L-Phenylalanine | <0.1 |
| L-Tryptophan | <0.1 |
| L-Proline | <0.1 |
| L-Lysine | <0.1 |
| L-Ornithine | <0.1 |
| L-Histidine | <0.1 |
| L-Arginine | <0.1 |
| L-Cysteine | <0.1 |
| L-Methionine | <0.1 |

When the above sensor was preserved in 0.02M phosphate buffer at 3° C., and responses to sodium L-glutamate solutions were measured similarly as described above on the respective elapsed days, it was found that the initial response was maintained over one month. Thus, the above immobilized enzyme membrane is stable for at least one month at 3° C.

EXAMPLE C2

The immobilized Cellophane membrane of L-glutamic acid oxidase obtained according to the same procedure as in Example C1 was cut into a piece of circular shape, which was mounted on an electrode of a hydrogen peroxide electrode (produced by Ishikawa Seisakusho Co., Ltd.), and further the immobilized enzyme membrane was covered with a cellulose dialyzing membrane to prepare an L-glutamic acid sensor which has the similar structure as that of the sensor prepared in Example C1. By the use of the above sensor, an L-glutamic acid analyzing device similar to the device of Example C1 was prepared.

Figure 22:
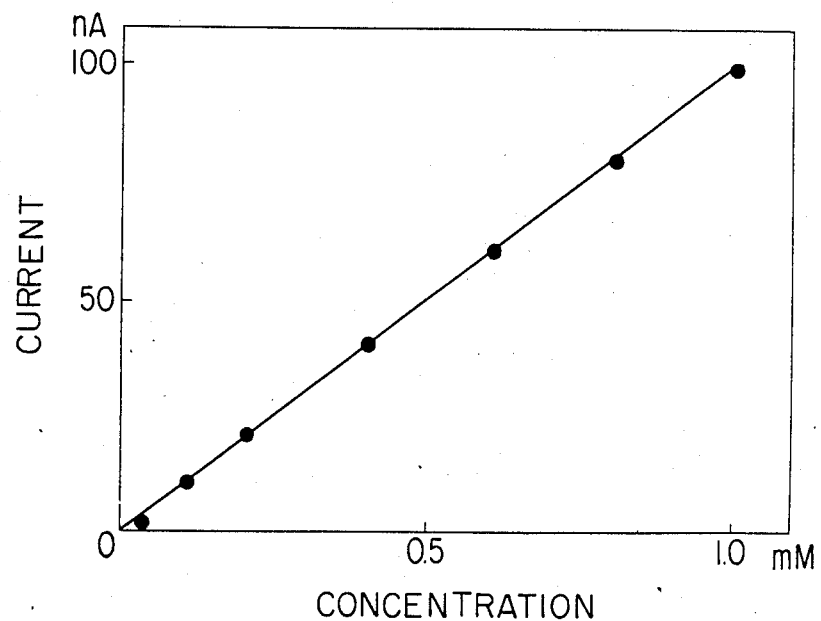
FIG. 22 is a graph showing the correlation between sodium L-glutamate concentration and the current value when the L-glutamic acid analyzer described in Example C2 is used.

Sodium L-glutamate standard solutions were injected into the above device for measurement of the current values, from which the correlation between sodium L-glutamate concentrations and the current values was obtained as shown in FIG. 22.

EXAMPLE C3

A commercially available soy sauce was diluted 10-fold with 0.1M phosphate buffer (pH 7.0) and subjected to bubbling with air to saturate oxygen. The above sample solution (1 ml) was injected into 49 ml of 0.1 M phosphate buffer (pH 7.0) and assayed by means of the device prepared in Example C1. From the current reduction value obtained, with reference to the calibration curve, the L-glutamic acid concentration of the soy sauce was calculated. It was found that this value coincided well with the quantitatively determined value obtained by a commercially available L-glutamic acid autoanalyzer (produced by Technicon Instruments Co.) in which measurement is carried out by the colorimetric method using an L-glutamic acid decarboxylase.

Figure 23:
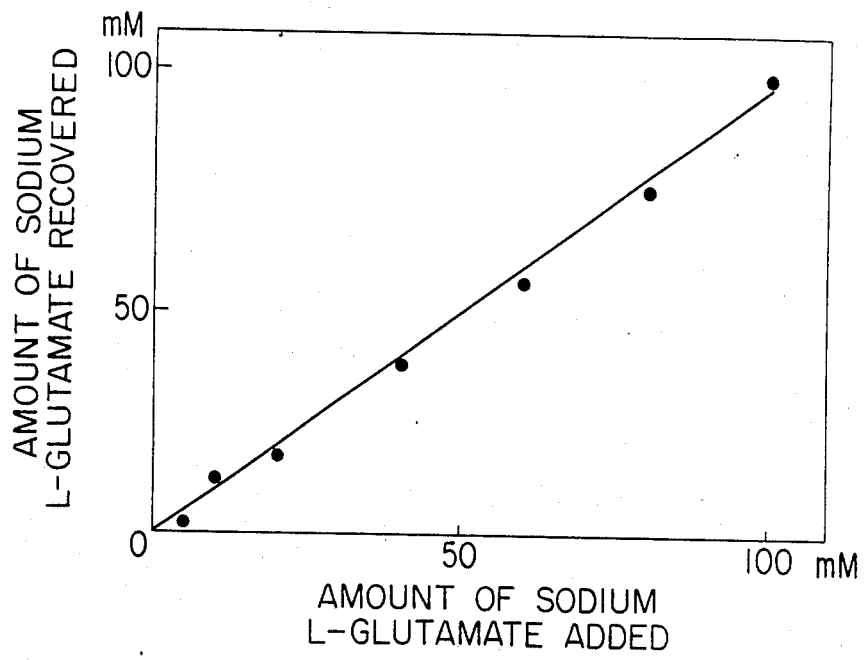
FIG. 23 is a graph showing the correlation between the amounts of sodium L-glutamate added to soy sauce and recovered when the device shown in FIG. 18 is used.
Figure 24:
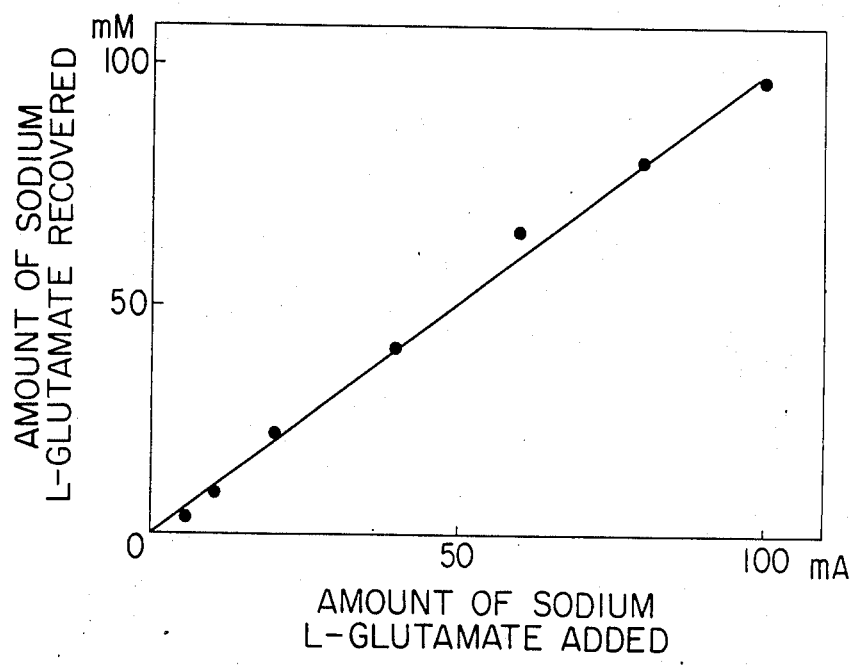
FIG. 24 is a graph showing the correlation between the amounts of sodium L-glutamate added to soy sauce and recovered when the L-glutamic acid analyzer described in Example C2 is used.

Further, to a commercially available soy sauce was added a given amount (5–100 mM) of sodium L-glutamate for examination of recovery thereof with the use of the devices of Example C1 and Example C2. With reference to the calibration curve for each device, the amount of sodium L-glutamate recovered was calculated. It was found that the amount was substantially in proportion to the amount of sodium L-glutamate added as shown in FIG. 23 (the device of Example C1) and FIG. 24 (the device of Example C2).

What is claimed is:

1. A method for analysis of L-glutamic acid, which comprises acting L-glutamic acid oxidase with L-glutamic acid in a sample to be analyzed in the presence of oxygen and water, and detecting the consumption of oxygen or the formation of hydrogen peroxide, ammonia or α-ketoglutaric acid accompanying the reaction, wherein said L-glutamic acid oxidase is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
   (a) stable in the pH range from 5.5 to 10.5 under maintenance conditions of 37° C. and 60 minutes;
   (b) stable in the temperature range of up to 65° C. under maintenance conditions of pH 5.5 and 15 minutes;
   (c) optimum activity in the pH range from 7 to 8.5;
   (d) is not inactivated by cupric chloride in a concentration of 1.0 mM at pH 7.4;
   (e) contains 2 mols of flavin adenine dinucleotide per mol of the oxidase as a coenzyme; and
   (f) a molecular weight of 135,000±10,000 as estimated by gel filtration.

2. A method for analysis of L-glutamic acid, which comprises reacting L-glutamic acid oxidase with L-glutamic acid at pH 5–6 in the presence of oxygen and water in a sample to be analyzed containing L-asparatic acid together with L-glutamic acid, and detecting the consumption of oxygen or the formation of hydrogen peroxide, ammonia or a α-ketoglutaric acid accompanying the reaction, wherein said L-glutamic acid oxidase is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
   (a) stable in the pH range from 5.5 to 10.5 under maintenance conditions of 37° C. and 60 minutes;
   (b) stable in the temperature range of up to 65° C. under maintenance conditions of pH 5.5 and 15 minutes;
   (c) optimum activity in the pH range from 7 to 8.5;

(d) is not inactivated by cupric chloride in a cocentration of 1.0 mM at pH 7.4;
(e) contains 2 mols of falvin adenine dinucleotide per mol of the oxidase as a coenzyme; and
(f) a molecular weight of 135,000±10,000 as estimated by gel filtration.

3. A reagent for analysis of L-glutamic acid, comprising an L-glutamic acid oxidase and a buffering agent suitable for use in enzymatic reaction,
wherein said L-glutamic acid oxidase is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
(a) stable in the pH range from 5.5 to 10.5 under maintenance conditions of 37° C. and 60 minutes;
(b) stable in the temperature range of up to 65° C. under maintenance conditions of pH 5.5 and 15 minutes;
(c) optimum activity in the pH range from 7 to 8.5;
(d) is not inactivated by cupric chloride in a concentration of 1.0 mM at pH 7.4;
(e) contains 2 mols of flavin adenine dinucleotide per mol of the oxidase as a coenzyme; and
(f) a molecular weight of 135,000±10,000 as estimated by gel filtration.

4. A reagent for analysis of L-glutamic acid, comprising an L-glutamic acid oxidase immobilized on a carrier,
wherein said L-glutamic acid oxidase is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
(a) stable in the pH range from 5.5 to 10.5 under maintenance conditions of 37° C. and 60 minutes;
(b) stable in the temperature range of up to 65° C. under maintenance conditions of pH 5.5 and 15 minutes;
(c) optimum activity in the pH range from 7 to 8.5;
(d) is not inactivated by cupric chloride in a concentration of 1.0 mM at pH 7.4;
(e) contains 2 mols of flavin adenine dinucleotide per mol of the oxidase as a coenzyme; and
(f) a molecular weight of 135,000±10,000 as estimated by gel filtration.

5. A kit for analysis of L-glutamic acid, comprising an L-glutamic acid oxidase and a detecting reagent for enyzmatic reaction,
wherein said L-glutamic acid oxidase is an L-amino acid oxidase having activity of oxidative deamination of the α-amino group of L-glutamic acid in the presence of water and oxygen to form α-ketogluatic acid, ammonia and hydrogen peroxide; having a substrate specificity for L-glutamic acid substantially without acting on L-glutamine and L-histidine; and having the following properties:
(a) stable in the pH range from 5.5 to 10.5 under maintenance conditions of 37° C. and 60 minutes;
(b) stable in the temperature range of up to 65° C. under maintenance conditions of pH 5.5 and 15 minutes;
(c) optimum activity in the pH range from 7 to 8.5;
(d) is not inactivated by cupric chloride in a concentration of 1.0 mM at pH 7.4;
(e) contains 2 mols of flavin adenine dinucleotide per mol of the oxidase as a coenzyme; and
(f) a molecular weight of 135,000±10,000 as estimated by gel filtration.

6. A kit according to claim 5 wherein the detecting reagent is a reagent for detection of hydrogen peroxide, ammonia or α-ketoglutaric acid.

7. A kit according to claim 5 wherein the detecting reagent is a single color forming agent or a combined reagent of a color forming agent and a coupler.

8. A biosensor comprising a receptor portion for a substance to be detected comprising an L-glutamic acid oxidase, and a transducer portion which detects chemical or physical change in a sample for analysis by the action of said L-glutamic acid oxidase and transduces it to an electrical signal,
wherein said L-glutamic acid oxidase is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
(a) stable in the pH range from 5.5 to 10.5 under maintenance conditions of 37° C. and 60 minutes;
(b) stable in the temperature range of up to 65° C. under maintenance conditions of pH 5.5 and 15 minutes;
(c) optimum activity in the pH range from 7 to 8.5;
(d) is not inactivated by cupric chloride in a concentration of 1.0 mM at pH 7.4;
(e) contains 2 mols of falvin adenine dinucleotide per mol of the oxidase as a coenzyme; and
(f) a molecular weight of 135,000±10,000 as estimated by gel filtration.

9. A biosensor according to claim 8 wherein the transducer portion is an electrode which detects a chemical change in the sample and transduces it to an electrical signal.

10. A biosensor according to claim 8 wherein the receptor portion comprises immobilized L-glutamic acid oxidase.

* * * * *